(12) United States Patent
Kozloski et al.

(10) Patent No.: US 12,005,256 B2
(45) Date of Patent: Jun. 11, 2024

(54) ADJUSTMENT OF ANALGESIC STIMULATION PARAMETERS BASED ON TRUST DYNAMIC MEASUREMENTS

(71) Applicant: Boston Scientific Neuromodulation Corporation, Valencia, CA (US)

(72) Inventors: James R. Kozloski, New Fairfield, CT (US); Anup Kalia, Elmsford, NY (US); Jeffrey Rogers, Briarcliff Manor, NY (US); Sara E. Berger, White Plains, NY (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/218,951

(22) Filed: Jul. 6, 2023

(65) Prior Publication Data
US 2023/0347151 A1    Nov. 2, 2023

Related U.S. Application Data

(63) Continuation of application No. 17/536,351, filed on Nov. 29, 2021, now Pat. No. 11,745,016, which is a
(Continued)

(51) Int. Cl.
*A61N 1/00*      (2006.01)
*A61N 1/02*      (2006.01)
(Continued)

(52) U.S. Cl.
CPC ......... *A61N 1/36132* (2013.01); *A61N 1/025* (2013.01); *A61N 1/36071* (2013.01);
(Continued)

(58) Field of Classification Search
None
See application file for complete search history.

(56) References Cited

U.S. PATENT DOCUMENTS

| | | |
|---|---|---|
| 11,219,765 B2 | 1/2022 | Kozloski et al. |
| 2002/0042563 A1 | 4/2002 | Becerra et al. |
| (Continued) | | |

FOREIGN PATENT DOCUMENTS

| | | |
|---|---|---|
| AU | 2019272566 B2 | 5/2022 |
| WO | WO-2019226557 A1 | 11/2019 |

OTHER PUBLICATIONS

Losin, Elizabeth A. Reynolds, et al. "Feelings of Clinician-Patient Similarity and Trust Influence Pain: Evidence From Simulated Clinical Interactions." The Journal of Pain, vol. 18, No. 7, 2017, pp. 787-799. doi:10.1016/j.jpain.2017.02.428 (Year: 2017).*

(Continued)

*Primary Examiner* — John R Downey
*Assistant Examiner* — Anant A Gupta
(74) *Attorney, Agent, or Firm* — Schwegman Lundberg & Woessner, P.A.

(57) ABSTRACT

Systems and techniques are disclosed to establish programming of an implantable electrical neurostimulation device for treating pain of a human subject, through the use and adjustment of analgesic stimulation parameters based on trust dynamics and trust measurements. In an example, the system to establish programming of the neurostimulation device performs operations that: determine a trust measurement value that is derived from results of at least one commitment made with a human subject, via observable interactions; determine a modification of at least one neurostimulation programming parameter, based on the trust measurement value; and to cause the implantable neurostimulation device to implement the modification of the at least one neurostimulation programming parameter. Further examples are provided to produce and track the trust measurement value, as well as identify a pain susceptibility
(Continued)

value and determine a receptiveness to analgesic effects based on these and other trust dynamics.

20 Claims, 8 Drawing Sheets

Related U.S. Application Data continuation of application No. 16/417,577, filed on May 20, 2019, now Pat. No. 11,219,765.

(60) Provisional application No. 62/675,000, filed on May 22, 2018.

(51) Int. Cl.
    *A61N 1/36* (2006.01)
    *G16H 20/40* (2018.01)
(52) U.S. Cl.
    CPC ..... *A61N 1/36135* (2013.01); *A61N 1/36175* (2013.01); *A61N 1/36189* (2013.01); *G16H 20/40* (2018.01)

(56) References Cited

U.S. PATENT DOCUMENTS

| | | | |
|---|---|---|---|
| 2011/0270358 | A1 | 11/2011 | Davis et al. |
| 2013/0317941 | A1 | 11/2013 | Stoll et al. |
| 2015/0317447 | A1 | 11/2015 | Helleputte et al. |
| 2015/0327802 | A1 | 11/2015 | Miyake |
| 2016/0256690 | A1 | 9/2016 | Cecchi et al. |
| 2017/0056641 | A1 | 3/2017 | Bochenko |
| 2017/0056642 | A1* | 3/2017 | Moffitt ............... A61N 1/36071 |
| 2017/0080233 | A1 | 3/2017 | Torgerson et al. |
| 2018/0043172 | A1* | 2/2018 | Serrano Carmona ....................... A61N 1/36132 |
| 2018/0104493 | A1 | 4/2018 | Doan et al. |
| 2019/0358457 | A1 | 11/2019 | Kozloski et al. |
| 2022/0080204 | A1 | 3/2022 | Kozloski et al. |

OTHER PUBLICATIONS

Kalia, Anup K., "Combining Trust with Risk, Commitments, and Emotions", TRACE: A Dynamic Model of Trust for People-Driven Service Engagements, NC State University meeting Sep. 30, 2015; Slide Presentation, (Sep. 2015), 24 slides (Year: 2015).*
"U.S. Appl. No. 16/417,577, 312 Amendment filed Nov. 29, 2021", 9 pgs.
"U.S. Appl. No. 16/417,577, Corrected Notice of Allowability dated Sep. 20, 2021", 5 pgs.
"U.S. Appl. No. 16/417,577, Corrected Notice of Allowability dated Dec. 9, 2021", 4 pgs.
"U.S. Appl. No. 16/417,577, Examiner Interview Summary dated May 21, 2021", 3 pgs.
"U.S. Appl. No. 16/417,577, Non Final Office Action dated Feb. 16, 2021", 19 pgs.
"U.S. Appl. No. 16/417,577, Notice of Allowance dated Sep. 1, 2021", 10 pgs.
"U.S. Appl. No. 16/417,577, Response filed May 17, 2021 to Non Final Office Action dated Feb. 16, 2021", 15 pgs.
"U.S. Appl. No. 17/536,351, Non Final Office Action dated Dec. 22, 2022", 11 pgs.
"U.S. Appl. No. 17/536,351, Notice of Allowance dated Apr. 19, 2023", 10 pgs.
"U.S. Appl. No. 17/536,351, Response filed Mar. 22, 2023 to Non Final Office Action dated Dec. 22, 2022", 9 pgs.
"Australian Application Serial No. 2019272566, First Examination Report dated Jul. 23, 2021", 3 pgs.
"Australian Application Serial No. 2019272566, Response filed Apr. 22, 2022 to Subsequent Examiners Report dated Jan. 5, 2022", 24 pgs.
"Australian Application Serial No. 2019272566, Response filed Nov. 30, 2021 to First Examination Report dated Jul. 23, 2021", 17 pgs.
"Australian Application Serial No. 2019272566, Subsequent Examiners Report dated Jan. 5, 2022", 3 pgs.
"Canadian Application Serial No. 3,099,520, Examiner's Rule 86(2) Report dated Aug. 5, 2022", 4 pgs.
"Canadian Application Serial No. 3,099,520, Office Action dated Nov. 5, 2021", 5 pgs.
"Canadian Application Serial No. 3,099,520, Response filed Mar. 4, 2022 to Office Action dated Nov. 5, 2021", 30 pgs.
"Canadian Application Serial No. 3,099,520, Response filed Nov. 10, 2022 to Examiner's Rule 86(2) Report dated Aug. 5, 2022", 23 pgs.
"European Application Serial No. 19728835.0, Response filed Jul. 21, 2021 to Communication pursuant to Rules 161(1) and 162 EPC dated Jan. 19, 2021", 15 pgs.
"International Application Serial No. PCT/US2019/033142, International Preliminary Report on Patentability dated Dec. 3, 2020", 9 pgs.
"International Application Serial No. PCT/US2019/033142, International Search Report dated Sep. 11, 2019", 5 pgs.
"International Application Serial No. PCT/US2019/033142, Written Opinion dated Sep. 11, 2019", 7 pgs.
Baker, Tamara A., et al., "Experience and Knowledge of Pain Management in Patients Receiving Outpatient Cancer Treatment: What Do Older Adults Really Know about Their Cancer Pain?", Pain Medicine, vol. 15, Issue 1, (Jan. 2014), 52-60.
Baliki, M. N., et al., "Predicting value of pain and analgesia: nucleus accumbens response to noxious stimuli changes in the presence of chronic pain", Neuron, vol. 66, Issue 1, (Apr. 2010), 149-160.
Buchman, Daniel Z., et al., "You Present like a Drug Addict: Patient and Clinician Perspectives on Trust and Trustworthiness in Chronic Pain Management", Pain Medicine, vol. 17, Issue 8, (Aug. 2016), 1394-1406.
Colloca, Luana, et al., "Placebo analgesia induced by social observational learning", Pain, vol. 144, (Jan. 2009), 28-34.
Fett, Anne-Kathrin J., et al., "Default distrust? An fMRI investigation of the neural development of trust and cooperation", Scan, vol. 9, Issue 4, (Apr. 2014), 395-402.
Geers, Andrew L., et al., "Reconsidering the role of personality in placebo effects: Dispositional optimism, situational expectations, and the placebo response", Journal of Psychosomatic Research, vol. 58, Issue 2, copyright Elsevier Inc. doi:10.1016/j.jpsychores.2004.08.011, (Feb. 2005), 121-127.
Getov, Spas, et al., "Human brain structure predicts individual differences in preconscious evaluation of facial dominance and trustworthiness", Scan, vol. 10, Issue 5, (May 2015), 690-699.
Hashmi, Javeria A., et al., "Brain networks predicting placebo analgesia in a clinical trial for chronic back pain", Pain, vol. 153, Issue 12, (Dec. 2012), 2393-2402.
Hashmi, Javeria A., et al., "Shape shifting pain: chronification of back pain shifts brain representation from nociceptive to emotional circuits", Brain A Journal of Neurology, No. 136, (Sep. 2013), 2751-2768.
Hensel, Lukas, et al., "Neural Correlates of Explicit Social Judgments on Vocal Stimuli", Cerebral Cortex, vol. 25, Issue 5, (May 2015), 1152-1162.
Hyland, Michael E., et al., "Dispositional predictors of placebo responding: A motivational interpretation of flower essence and gratitude therapy", Journal of Psychosomatic Research, vol. 62, Issue 3, (Mar. 2007), 331-340.
Kalia, Anup K., "Combining Trust with Risk, Commitments, and Emotions", Trace: A Dynamic Model of Trust for People-Driven Service Engagements, NC State University meeting Sep. 30, 2015; Slide Presentation, (Sep. 2015), 24 slides.
Kalia, Anup K, et al., "Estimating Trust from Agents' Interactions via Commitments", NC State University, Raleigh, US, 2 pgs.
Kalia, Anup K., et al., "Guven: estimating trust from communications", Journal of Trust Management, vol. 3, Issue 1, (2016+), 19 pgs.

(56) References Cited

OTHER PUBLICATIONS

Kalia, Anup K, et al., "Trustworthy Decision Making via Commitments", This research was partially supported by the US Army Research Office under the Science of Security Lablet grant., 12 pgs.

Kalia, Anup Kumar, "Understanding Human Communication to Estimate Trust, Hierarchy, and Performance", Dissertation submitted to the Graduate Faculty of North Carolina State University, (2016), 155 pgs.

Losin, Elizabeth A, et al., "Feelings of Clinician-Patient Similarity and Trust Influence Pain: Evidence From Simulated Clinical Interactions", The Journal of Pain, vol. 18, No. 7, (2017), 787-799.

Lount Jr., Robert B., et al., "The Impact of Positive Mood on Trust in Interpersonal and Intergroup Interactions", Journal of Personality and Social Psychology, vol. 98, Issue 3, (Mar. 2010), 420-433.

Mansour, Ali, et al., "Brain white matter structural properties predict transition to chronic pain", Pain, vol. 154, Issue 10, (Oct. 2013), 2160-2168.

Mattavelli, Giulia, et al., "Response of face-selective brain regions to trustworthiness and gender of faces", Neuropsychologia, vol. 50, Issue 9, (Jul. 2012), 2205-2211.

Molton, Ivan R., et al., "Overview of Persistent Pain in Older Adults", American Psychologist, vol. 69, Issue 2, (Feb. 2014), 197-207.

Moore, Rhonda J., et al., "Handbook of Pain and Palliative Care—Biobehavioral Approaches for the Life Course", Department of Health and Human Services, Rockville, MD, USA, (2012), 863 pgs.

Mutso, Amelia A., et al., "Reorganization of hippocampal functional connectivity with transition to chronic back pain", Journal of Neurophysiology, vol. 111, Issue 5, (Mar. 2014), 1065-1076.

Pecina, Marta, et al., "Personality Trait Predictors of Placebo Analgesia and Neurobiological Correlates", Neuropsychopharmacology, vol. 38, Issue 4, (Mar. 2013), 639-646.

Pinto, Rafael Zambelli, et al., "Patient-centred communication is associated with positive therapeutic alliance: a systematic review", Journal of Physiotherapy, vol. 58, Issue 2, (2012), 77-87.

Sessa, Paola, et al., "Perceived trustworthiness shapes neural empathic responses toward others' pain", Neuropsychologia, vol. 79, Part A, (Dec. 2015), 97-105.

Sprengelmeyer, Reiner, et al., "The insular cortex and the neuroanatomy of major depression", Journal of Affective Disorders, vol. 133 (1-2), (Sep. 2011), 120-127.

Tetreault, Pascal, "Brain Connectivity Predicts Placebo Response across Chronic Pain Clinical Trials", Plos Biology, vol. 14, Issue 10, (Oct. 2016), 22 pgs.

Tsukiura, Takashi, et al., "Insular and hippocampal contributions to remembering people with an impression of bad personality", Scan, vol. 8, Issue 5, (Jun. 2013), 515-522.

Tuttle, Alexander H., et al., "Increasing placebo responses over time in U.S. clinical trials of neuropathic pain", Pain, vol. 156, Issue 12, (Dec. 2015), 2616-2626.

Vachon-Presseau, Etienne, et al., "Corticolimbic anatomical characteristics predetermine risk for chronic pain", Brain, vol. 139, Pt 7, (Jul. 2016), 1958-1970.

\* cited by examiner

ADJUSTMENT OF ANALGESIC STIMULATION PARAMETERS BASED ON TRUST DYNAMIC MEASUREMENTS

CLAIM OF PRIORITY

This application is a continuation of and claims the benefit of priority of U.S. patent application Ser. No. 17/536,351, filed Nov. 29, 2021, which is a continuation of and claims the benefit of priority of U.S. patent application Ser. No. 16/417,577, filed May 20, 2019, which claims the benefit of priority under 35 U.S.C. § 119(e) of U.S. Provisional Patent Application Ser. No. 62/675,000, filed on May 22, 2018, and titled "ADJUSTMENT OF ANALGESIC STIMULATION PARAMETERS BASED ON TRUST DYNAMIC MEASUREMENTS", which are incorporated by reference herein in their entireties.

DISCLAIMER

The claims and scope of the subject application, and any continuation, divisional or continuation-in-part applications claiming priority to the subject application, are solely limited to embodiments (e.g., systems, apparatus, methodologies, computer program products and computer readable storage media) directed to implanted electrical stimulation for pain treatment and/or management.

STATEMENT REGARDING JOINT RESEARCH AND DEVELOPMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

TECHNICAL FIELD

The present disclosure relates generally to medical devices, and more particularly, to systems, devices, and methods for electrical stimulation programming techniques, to perform implanted electrical stimulation for pain treatment and/or management.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neuromodulation system can be used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to create an analgesic effect that masks pain sensation. While modern electronics can accommodate the need for generating and delivering stimulation energy in a variety of forms, the capability of a neurostimulation system depends on its post-manufacturing programmability to a great extent. For example, a sophisticated neurostimulation program may only benefit a patient when it is customized for that patient, and stimulation patterns or programs of patterns that are predetermined at the time of manufacturing may substantially limit the potential for the customization.

SUMMARY

The following Summary provides examples as an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Example 1 is a system for use to adjust programming of an implantable electrical neurostimulation device for treating pain, the system comprising: at least one processor; and at least one memory device comprising instructions, which when executed by the processor, cause the processor to perform operations that: determine a trust measurement value, the trust measurement value being derived from results of at least one commitment made with a human subject, and the at least one commitment being associated with a plurality of interactions with the human subject; determine a modification of at least one neurostimulation programming parameter of the implantable neurostimulation device, based on the trust measurement value; and provide instructions to cause the implantable neurostimulation device to implement the modification of the at least one neurostimulation programming parameter.

In Example 2, the subject matter of Example 1 includes, the trust measurement value being further derived from a reaction of the human subject to a fulfillment or a violation of the at least one commitment, and wherein the trust measurement value is determined with a classifier that performs analysis of the plurality of interactions for the fulfillment or the violation of the at least one commitment, the classifier being trained to predict a trust disposition for the human subject towards an other entity during the plurality of interactions.

In Example 3, the subject matter of Example 2 includes, an amount of the modification of the at least one neurostimulation programming parameter from a first state to a second state being correlated to an amount of change in the trust measurement value from a first state to a second state.

In Example 4, the subject matter of Examples 2-3 includes, the plurality of interactions being performed with text or voice conversations occurring between the human subject and the other entity, wherein the other entity creates the commitment with the human subject and performs at least one observable action to cause the fulfillment or the violation of the at least one commitment.

In Example 5, the subject matter of Example 4 includes, the trust measurement value being representable as a value within a trust graph, wherein the trust graph provides a measurement of trust between the human subject and the other entity, based on evaluation of the human subject with the plurality of interactions over a period of time.

In Example 6, the subject matter of Examples 2-5 includes, further operations that: identify a pain susceptibility value applicable to the human subject, based on the trust measurement value derived from the at least one commitment; wherein the pain susceptibility value is based at least in part on a prediction of the trust disposition for the human subject towards the other entity; and wherein the modification of at least one neurostimulation programming parameter of the implantable neurostimulation device, is further based on the pain susceptibility value.

In Example 7, the subject matter of Example 6 includes, the operations to identify the pain susceptibility value for the human subject being further based on an identification of a pain measurement value derived from a neuroimaging procedure performed on the human subject.

In Example 8, the subject matter of Example 7 includes, the identification of the pain measurement value being derived from the neuroimaging procedure is used to determine a baseline to predict a placebo response of modification of the at least one neurostimulation programming parameter.

In Example 9, the subject matter of Examples 1-8 includes, the results of at least one commitment being determined from an observation of a reaction of the human subject to a violation or fulfillment of the at least one commitment, and wherein the observation of the reaction is determined from the plurality of interactions with the human subject.

In Example 10, the subject matter of Examples 1-9 includes, further operations that: determine a subsequent trust measurement metric, the subsequent trust measurement metric being determined from a series of interactions with the human subject conducted after the modification of the at least one neurostimulation programming parameter; determine a subsequent modification of the at least one neurostimulation programming parameter of the implantable neurostimulation device, based on the subsequent trust measurement metric; and provide instructions to cause the implantable neurostimulation device to implement the subsequent modification of the at least one neurostimulation programming parameter.

In Example 11, the subject matter of Examples 1-10 includes, the modification of the at least one neurostimulation programming parameter causing a change for one or more of: pulse patterns, pulse shapes, a spatial location of pulses, waveform shapes, or a spatial location of waveform shapes, for modulated energy provided with a plurality of leads of the implantable neurostimulation device.

In Example 12, the subject matter of Examples 1-11 includes, the modification of the at least one neurostimulation programming parameter being provided in a neurostimulation program for the implantable neurostimulation device, with further operations to update the neurostimulation program based on the modification of the at least one neurostimulation programming parameter.

In Example 13, the subject matter of Examples 1-12 includes, the implantable neurostimulation device being further configured to treat pain by delivering at least one of: an electrical spinal cord stimulation, an electrical brain stimulation, or an electrical peripheral nerve stimulation, in the human subject.

Example 14 is a machine-readable medium including instructions, which when executed by a machine, cause the machine to perform the operations of the system of any of the Examples 1 to 13.

Example 15 is a method to perform the operations of the system of any of the Examples 1 to 13.

Example 16 is a device for use to adjust programming of an implantable electrical neurostimulation device for treating pain, the device comprising: at least one processor and at least one memory; data measurement processing circuitry, operable with the processor and the memory, the data measurement processing circuitry configured to determine a trust measurement value from results of at least one commitment made with a human subject, with the at least one commitment being associated with a plurality of interactions with the human subject; neurostimulation programming circuitry, in operation with the at least one processor and the at least one memory, configured to: determine a modification of at least one neurostimulation programming parameter of the implantable neurostimulation device, based on the trust measurement value; and provide instructions to cause the implantable neurostimulation device to implement the modification of the at least one neurostimulation programming parameter.

In Example 17, the subject matter of Example 16 includes, the data measurement processing circuitry further configured to: determine the trust measurement value from a reaction of the human subject to a fulfillment or a violation of the at least one commitment; wherein the trust measurement value is determined with a classifier that performs analysis of the plurality of interactions for the fulfillment or the violation of the at least one commitment, and wherein the classifier is trained to predict a trust disposition for the human subject towards an other entity during the plurality of interactions.

In Example 18, the subject matter of Example 17 includes, an amount of the modification of the at least one neurostimulation programming parameter from a first state to a second state being correlated to an amount of change in the trust measurement value from a first state to a second state.

In Example 19, the subject matter of Examples 17-18 includes, the plurality of interactions being performed with text or voice conversations occurring between the human subject and the other entity, wherein the other entity creates the commitment with the human subject and performs at least one observable action to cause the fulfillment or the violation of the at least one commitment.

In Example 20, the subject matter of Examples 17-19 includes, the trust measurement value being representable as a value within a trust graph, wherein the trust graph provides a measurement of trust between the human subject and the other entity, based on evaluation of the human subject with the plurality of interactions over a period of time.

In Example 21, the subject matter of Examples 17-20 includes, the data measurement processing circuitry further configured to: identify a pain susceptibility value applicable to the human subject, based on the trust measurement value derived from the at least one commitment; wherein the pain susceptibility value is based at least in part on a prediction of the trust disposition for the human subject towards the other entity; and wherein the modification of at least one neurostimulation programming parameter of the implantable neurostimulation device, is further based on the pain susceptibility value.

In Example 22, the subject matter of Example 21 includes, the operations to identify the pain susceptibility value for the human subject being further based on an identification of a pain measurement value derived from a neuroimaging procedure performed on the human subject; and wherein the identification of the pain measurement value derived from the neuroimaging procedure is used to determine a baseline to predict a placebo response of modification of the at least one neurostimulation programming parameter.

In Example 23, the subject matter of Examples 16-22 includes, the results of at least one commitment being determined from an observation of a reaction of the human subject to a violation or fulfillment of the at least one commitment, and wherein the observation of the reaction is determined from the plurality of interactions with the human subject.

In Example 24, the subject matter of Examples 16-23 includes, the data measurement processing circuitry further configured to: determine a subsequent trust measurement metric, the subsequent trust measurement metric being determined from a series of interactions with the human subject conducted after the modification of the at least one neurostimulation programming parameter; determine a subsequent modification of the at least one neurostimulation programming parameter of the implantable neurostimulation device, based on the subsequent trust measurement metric; and provide instructions to cause the implantable neurostimulation device to implement the subsequent modification of the at least one neurostimulation programming parameter.

In Example 25, the subject matter of Examples 16-24 includes, the modification of the at least one neurostimulation programming parameter being provided in a neurostimulation program for the implantable neurostimulation device, wherein the neurostimulation programming circuitry is further configured to: update the neurostimulation program based on the modification of the at least one neurostimulation programming parameter; wherein the modification of the at least one neurostimulation programming parameter causes a change for one or more of: pulse patterns, pulse shapes, a spatial location of pulses, waveform shapes, or a spatial location of waveform shapes, for modulated energy provided with a plurality of leads of the implantable neurostimulation device.

Example 26 is a method for use to adjust programming of an implantable electrical neurostimulation device for treating pain, the method comprising a plurality of operations executed with at least one processor of an electronic device, the plurality of operations comprising: identifying a trust measurement value, the trust measurement value being derived from results of at least one commitment made with a human subject, and the at least one commitment being associated with a plurality of interactions with the human subject; determining a modification of at least one neurostimulation programming parameter of the implantable neurostimulation device, based on the trust measurement value; and causing the implantable neurostimulation device to implement the modification of the at least one neurostimulation programming parameter.

In Example 27, the subject matter of Example 26 includes: determining the trust measurement value from a reaction of the human subject to a fulfillment or a violation of the at least one commitment; wherein the trust measurement value is determined with a classifier that performs analysis of the plurality of interactions for the fulfillment or the violation of the at least one commitment, and wherein the classifier is trained to predict a trust disposition for the human subject towards an other entity during the plurality of interactions.

In Example 28, the subject matter of Example 27 includes, an amount of the modification of the at least one neurostimulation programming parameter from a first state to a second state being correlated to an amount of change in the trust measurement value from a first state to a second state.

In Example 29, the subject matter of Examples 27-28 includes, the plurality of interactions being performed with text or voice conversations occurring between the human subject and the other entity, wherein the other entity creates the commitment with the human subject and performs at least one observable action to cause the fulfillment or the violation of the at least one commitment.

In Example 30, the subject matter of Examples 27-29 includes, the trust measurement value being representable as a value within a trust graph, and wherein the trust graph provides a measurement of trust between the human subject and the other entity, based on evaluation of the human subject with the plurality of interactions over a period of time.

In Example 31, the subject matter of Examples 27-30 includes: identifying a pain susceptibility value applicable to the human subject, based on the trust measurement value derived from the at least one commitment; wherein the pain susceptibility value is based at least in part on a prediction of the trust disposition for the human subject towards the other entity; and wherein the modification of at least one neurostimulation programming parameter of the implantable neurostimulation device, is further based on the pain susceptibility value.

In Example 32, the subject matter of Example 31 includes, wherein identifying the pain susceptibility value for the human subject is further based on an identification of a pain measurement value derived from a neuroimaging procedure performed on the human subject; and wherein the identification of the pain measurement value derived from the neuroimaging procedure is used to determine a baseline to predict a placebo response of modification of the at least one neurostimulation programming parameter.

In Example 33, the subject matter of Examples 26-32 includes, the results of at least one commitment being determined from an observation of a reaction of the human subject to a violation or fulfillment of the at least one commitment, wherein the observation of the reaction is determined from the plurality of interactions with the human subject.

In Example 34, the subject matter of Examples 26-33 includes: identifying a subsequent trust measurement metric, the subsequent trust measurement metric being identified from a series of interactions with the human subject conducted after the modification of the at least one neurostimulation programming parameter; determining a subsequent modification of the at least one neurostimulation programming parameter of the implantable neurostimulation device, based on the subsequent trust measurement metric; and causing the implantable neurostimulation device to implement the subsequent modification of the at least one neurostimulation programming parameter.

In Example 35, the subject matter of Examples 26-34 includes, the modification of the at least one neurostimulation programming parameter being provided in a neurostimulation program for the implantable neurostimulation device, with the operations further comprising: updating the neurostimulation program based on the modification of the at least one neurostimulation programming parameter; wherein the modification of the at least one neurostimulation programming parameter causes a change for one or more of: pulse patterns, pulse shapes, a spatial location of pulses, waveform shapes, or a spatial location of waveform shapes, for modulated energy provided with a plurality of leads of the implantable neurostimulation device.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
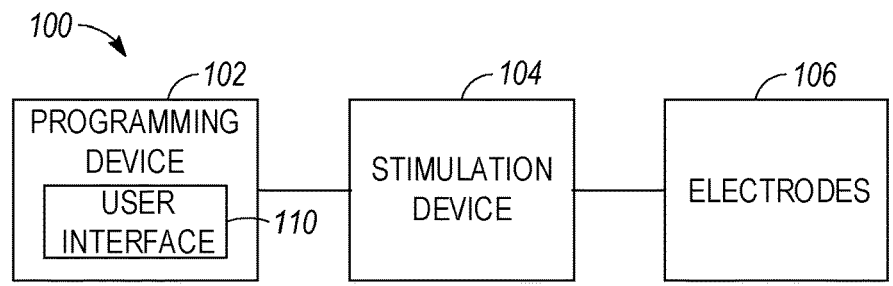
FIG. 1 illustrates, by way of example, an embodiment of a neurostimulation system.

This document discusses various techniques that can generate programming of an implantable electrical neurostimulation device, for the treatment of pain of a human subject (e.g., a patient). As an example, various systems and methods are described to adjust analgesic stimulation parameters of neurostimulation treatment based on a measure of trust dynamics. These systems and methods are designed to exploit a measure of trust disposition in a subject patient to deliver or modify neurostimulation treatment that is associated with an expected pain response. Specifically, the relationship between trust and pain (and a patient's response to pain treatments) is exploited so that suitable adjustments can be made to the amount, type, and characteristics of neurostimulation treatment that cause analgesic (e.g., pain-decreasing, masking) effects in a patient.

Chronic pain is a common condition for many patients, but a condition which may be addressed through the use of neurostimulation therapy (e.g., electrical spinal cord stimulation, electrical peripheral nerve stimulation, or electrical brain stimulation) to deliver treatment. One limiting factor for existing applications of neurostimulation therapies is that, even if a number of advanced programs can be applied by a neurostimulation device, patients often only end up using very few of the available treatments (e.g., two or three programs) suggested by a clinician or other medical professional. As a result, the treatment results are often not effective and the patient ends up applying programs that are not customized to the patient or a best fit for the patient's current state. The present techniques and systems improve this scenario through the use of a program modeling system adaptive to the trust state of the patient. This program modeling system is able to modify neurostimulation programs and program parameters that are appropriate for a patient based on the patient's state of pain, the patient's susceptibility to pain, the patient's likelihood of responding to pain treatment, and other characteristics that are derivable or tied to trust measurements and trust disposition. These trust measurements and trust disposition are in turn determined by the observation or measurement of interactions and commitments made in such interactions. As a result, a scientific and objective way of measuring and predicting trust in a patient can lead to new types of neurostimulation treatments and treatment results.

The program modeling system discussed herein enables the adaptation of neurostimulation parameters based on multiple aspects of pain measurements, including pain susceptibility, treatment susceptibility, predicted treatment effectiveness, and patient feedback, all tied to trust measures or trust predictions. The program modeling system provides a dynamic system that is responsive to the unique trust state of patient, which in turn is tied to the susceptibility of the patient to experience pain and/or respond to pain treatments. In an example, the program modeling system generates a modification of a neurostimulation programming parameter directly based on a trust measurement value. In other examples, the program modeling system converts the trust measurement value into a pain susceptibility value, and generates the modification of the neurostimulation programming parameter directly based on the pain susceptibility value. Other indirect measurements and evaluations of pain, trust, and treatment effectiveness may also be incorporated into the program modeling system.

The stimulator input produced by the program modeling system enables exploration of a set of possible neurostimulation programs and program settings that are expanded and adapted over time, as parameters are created, modified, or selected for the particular patient. These programming parameters may be arranged or defined (e.g., created, modified, activated, etc.) into new or updated sets of neurostimulation operational programs (also plainly referred to as "programs" in this document), resulting in an identification of a particular neurostimulation program that includes at least a portion of the pain treatment parameters identified as a best-fit for the human patient, given a particular state of trust, state of pain, and treatment objectives. The deployment and programming of these parameters and program(s) may be provided and monitored, with further feedback being collected on how successful a particular treatment is relative to the state of pain and the state of trust by the patient.

The trust modeling system disclosed herein employs a dynamical model to compute trust values based on an assessment of patient interactions with another human or automated entity. These interactions are observed as conditions are established, fulfilled, modified, and violated. These interactions may be simple or complex in nature (e.g., involving a simple promise made and immediately fulfilled by an agent, or a complex set of conditions and actions between multiple parties), and may occur in a variety of automated agent-based settings (e.g., with a chat bot or personal digital assistant) or human-based settings (e.g., discussion between two people, such as the patient and a clinician, nurse, or other agent). The state of trust of a patient may be determined in various examples with use of a trust classifier, including a classifier or classification model adapted from various forms of artificial intelligence, machine learning, or data structures. The state of trust or trust measurements of a patient also may be represented in a trust graph, neural network, or other advanced data structure. This classifier and trust graph may be trained over time to generate an ongoing prediction of trust values from future communication with the chatbot or others.

The techniques of this document enable automatic or human-driven improvements that create, establish, activate, select, modify, update, or adapt programming for a neurostimulation device (or to re-program a neurostimulation device) based on trust dynamics. These techniques accordingly improve pain treatment techniques and treatment efficacy of neurostimulation device usage, based on the particular physiological (and mental and emotional) state of a patient and the patient's receptiveness for treatment. Given the large number of permutations in neurostimulation output available in any given program, and the wide variation among different types of programs, such customization of neurostimulation parameters to a particular patient's pain state or pain susceptibility is not feasible with many existing approaches.

In an example, a parameter adjustment is initiated by the trust modeling system and program modeling system to dynamically select, adjust, and modify neurostimulation treatment that provides an analgesic effect correlated to pain and treatment states of a human subject. The programming selection, adjustment, and modification logic of the program modeling system operates to identify appropriate neurostimulation programming parameters using the previously described trust model, and identify values of the programming parameters that predict an improvement to pain treatment and a state of pain. Finally, the programming selection, adjustment, and modification logic of the program modeling system operates to collect feedback from subsequent conditions and changes in trust measurements, pain measurements, and susceptibility to treatment, to provide an ongoing treatment adjustment for the predicted state of the patient and the patient's chronic pain.

By way of example, operational parameters of the neurostimulation device may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and apply any number of control techniques to modify the electrical simulation applied to anatomical sites or systems related to pain or analgesic effect. In various embodiments, a neurostimulator program may include parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use.

In various embodiments, the present subject matter may be implemented using a combination of hardware and software designed to provide users such as patients, caregivers, clinicians, researchers, physicians, or others with the ability to generate, identify, select, implement, and update neurostimulation programs that provide analgesic effect for pain treatment of a human subject. The adaptation of such neurostimulation programs may result in variation in the location, intensity, and type of defined waveforms and patterns in an effort to increase therapeutic efficacy and/or patient satisfaction for neurostimulation therapies, including but not being limited to SCS and DBS therapies. While neurostimulation is specifically discussed as an example, the present subject matter may apply to any therapy that employs stimulation pulses of electrical or other forms of energy for treating chronic pain.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc. Accordingly, the following drawings provide an introduction to the features of an example neurostimulation system and how such programming may be accomplished through neurostimulation systems.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are programmable by a clinical user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. These adjustments may also include changing and editing values for the user-programmable parameters or sets of the user-programmable parameters individually (including values set in response to a therapy efficacy indication). Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

As described in more detail below with respect to FIGS. 7 to 9, a user, e.g., the patient, or a clinician or other medical professional associated with the patient can select, load, modify, and implement one or more parameters of a defined program for neurostimulation treatment, based on programming determination logic that identifies the parameters using a trust modeling system and a program modeling system. Based on a modeling of pain, the programming determination logic can determine which program or parameter is likely to produce an improvement for a predetermined condition involving chronic pain. Example parameters that can be implemented by a selected program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time).

Figure 6:
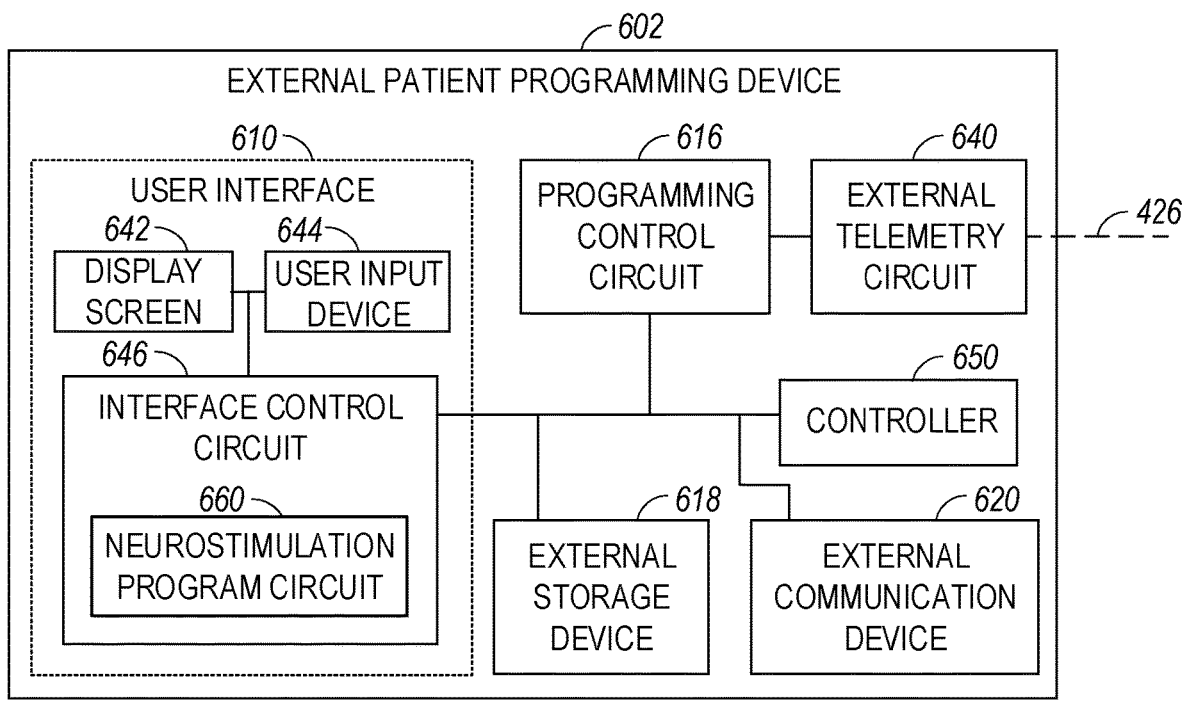
FIG. 6 illustrates, by way of example, an embodiment of a patient programming device for a neurostimulation system, such as the implantable neurostimulation system of FIG. 4.

As detailed in FIG. 6, a controller, e.g., controller 650 of FIG. 6, can implement program(s) and parameter setting(s) to implement a specific neurostimulation waveform, pattern, or energy output, using a program or setting in storage, e.g., external storage device 618 of FIG. 6, or using settings communicated via an external communication device 620 of FIG. 6 corresponding to the selected program. The implementation of such program(s) or setting(s) may further define a therapy strength and treatment type corresponding to a specific pulse group, or a specific group of pulse groups, based on the specific program(s) or setting(s). As also described in more detail below with respect to FIG. 7 and thereafter, a program modeling system and pain modeling logic may operate to produce this information based on trust dynamics. As also described, a clinician or the patient may also affect use and implementation of such programs or settings, including in settings where a combination of dynamic (automatic) and manual control are involved.

Portions of the stimulation device 104, e.g., implantable medical device, or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could also include a subcutaneous medical device (e.g., subcutaneous ICD, subcutaneous diagnostic device), wearable medical devices (e.g., patch based sensing device), or other external medical devices.

Figure 2:
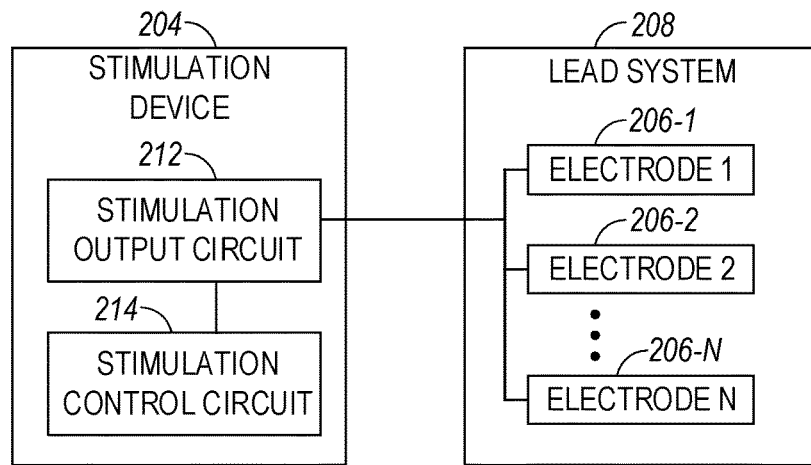
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, . . . electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power.

The neurostimulation system may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. Some examples are configured to determine a modulation parameter set to create a field shape to provide a broad and uniform modulation field such as may be useful to prime targeted neural tissue with sub-perception modulation. Some examples are configured to determine a modulation parameter set to create a field shape to reduce or minimize modulation of non-targeted tissue (e.g., dorsal column tissue). Various examples disclosed herein are directed to shaping the modulation field to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue. A benefit of MICC is that MICC accounts for various in electrode-tissue coupling efficiency and perception threshold at each individual contact, so that "hotspot" stimulation is eliminated.

The number of electrodes available combined with the ability to generate a variety of complex electrical pulses, presents a huge selection of available modulation parameter sets to the clinician or patient. For example, if the neurostimulation system to be programmed has sixteen electrodes, millions of modulation parameter value combinations may be available for programming into the neurostimulation system. Furthermore, SCS systems may have as many as thirty-two electrodes, which exponentially increases the number of modulation parameter value combinations available for programming. To facilitate such programming, a clinician often initially programs and modifies the modulation parameters through a computerized programming system, to allow the modulation parameters to be established from starting parameter sets (programs) and patient and clinician feedback. In addition, the patient often is provided with a limited set of controls to switch from a first program to a second program, based on user preferences and the subjective amount of pain or discomfort that the patient is treating. However, the implementation and use of a program modeling system and pain modeling logic as described further in FIGS. 7 to 9 and thereafter provides a mechanism for recommending and controlling programs with new combinations of parameter settings, in a fashion that emphasizes customization to the patient based on trust dynamics.

Figure 3:
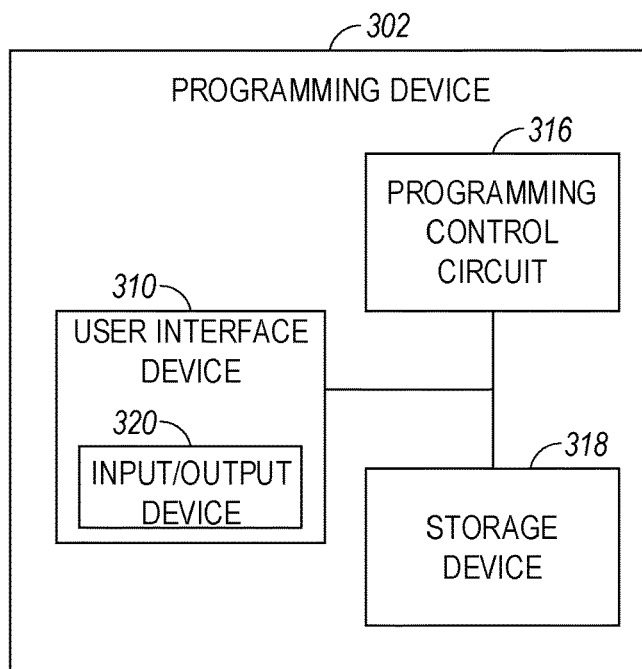
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), including values of a therapeutic neurostimulation field. In various examples, the user interface device 310 can receive user input to initiate the implementation of the programs which are recommended, modified, selected, or loaded through use of a program modeling system, which are described in more detail below.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings) loaded from a clinical encounter, managed from the patient feedback computing device, or stored in storage device 318 as templates. In various embodiments, the input/output device 320 and accompanying software on the user interface device 310 allows newly created building blocks, program components, programs, and program modifications to be saved, stored, or otherwise persisted in storage device 318.

In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs, and as applicable, to edit or modify waveforms, building blocks, and program components. Thus, the input/output device 320 may include one or more of a touchscreen, keyboard, keypad, touchpad, trackball, joystick, and mouse. In various embodiments, circuits of the neurostimulation system 100, including its various embodiments discussed in this document, may be implemented using a combination of hardware and software. For example, the logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
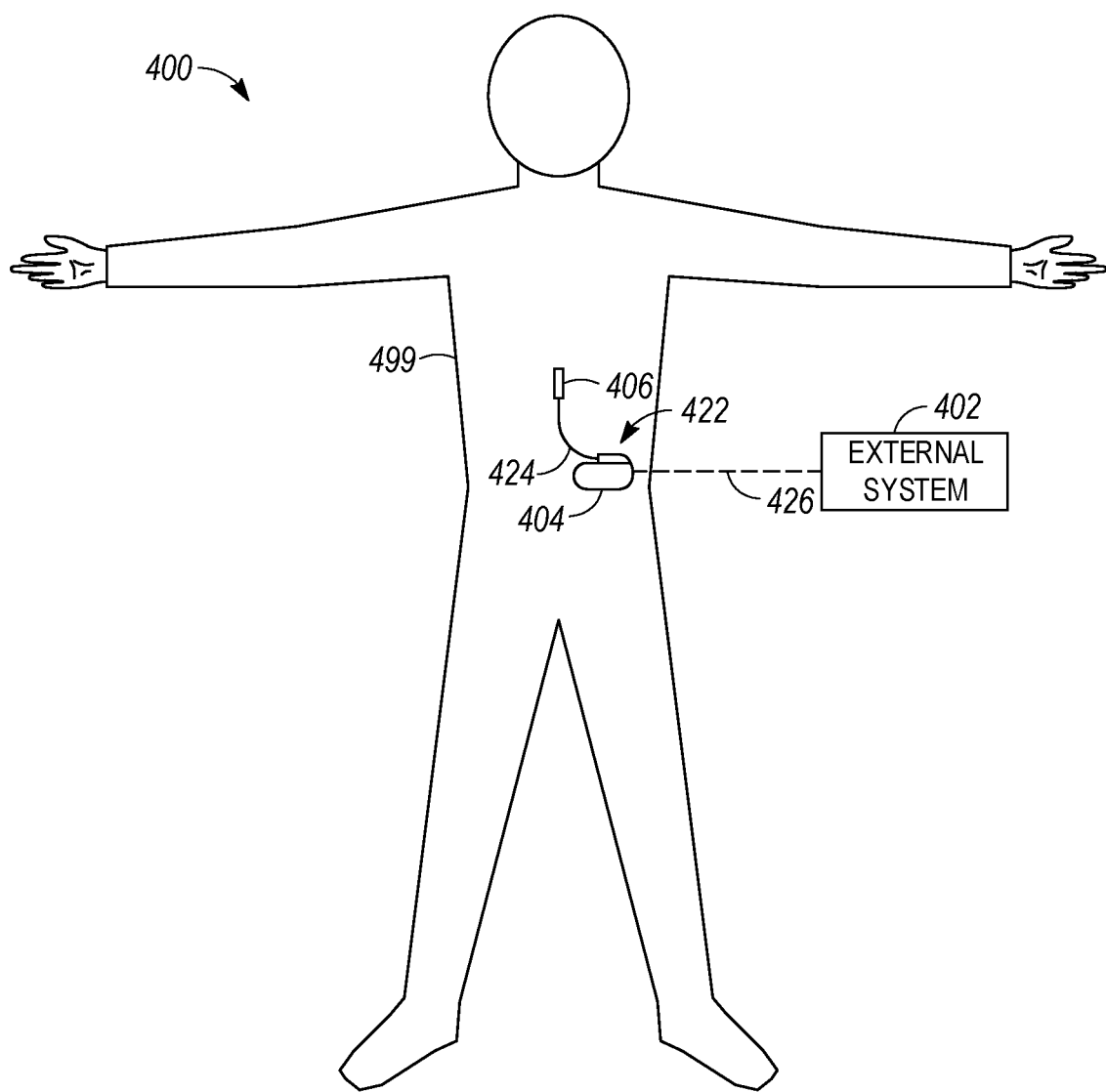
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, or manually obtained from user input entered in a user interface.

For the purposes of this specification, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuroplasticity or neurogenesis of tissue. It will be understood that other clinical effects and physiological mechanisms may also be provided through use of such stimulation techniques.

Figure 5:
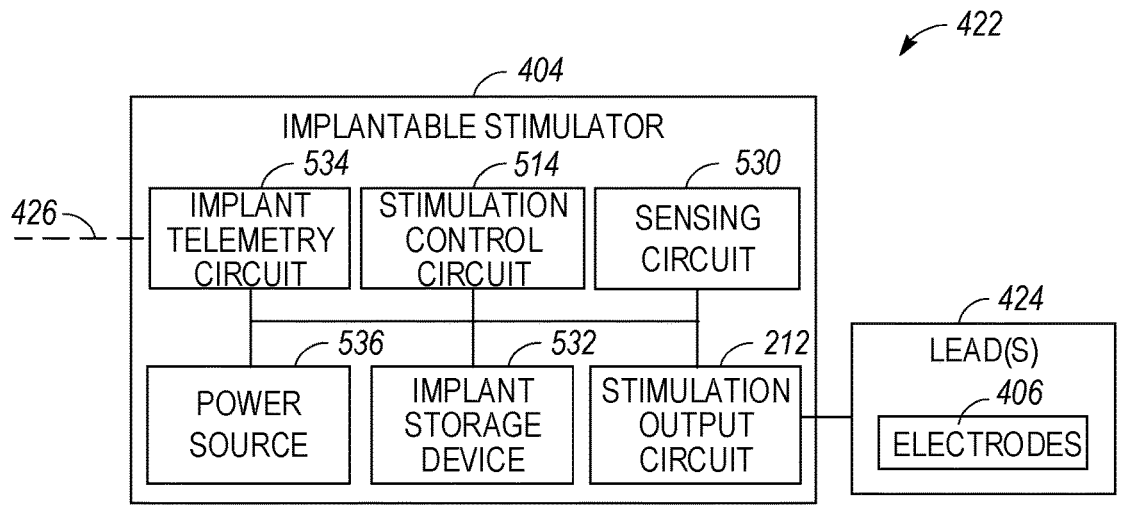
FIG. 5 illustrates, by way of example, an embodiment of an implantable stimulator and one or more leads of a neurostimulation system, such as the implantable neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 that is optional and required only when the stimulator has a sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a program selected with the present dynamic model or dynamical information system) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces. The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs obtained using the patient feedback and the programming modification logic techniques disclosed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530 (if included), the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

FIG. 6 illustrates an embodiment of an external patient programming device 602 of an implantable neurostimulation system, such as the external system 402, with the external patient programming device 602 illustrated to receive commands (e.g., program selections, information) directly or indirectly from a program modeling system (not shown in FIG. 6, but discussed with reference to FIGS. 7 to 9, below). The external patient programming device 602 represents an embodiment of the programming device 302, and includes an external telemetry circuit 640, an external storage device 618, a programming control circuit 616, a user interface device 610, a controller 650, and an external communication device 620.

The external telemetry circuit 640 provides the external patient programming device 602 with wireless communication to and from another controllable device such as the implantable stimulator 404 via the telemetry link 426, including transmitting one or a plurality of stimulation parameters (including changed stimulation parameters of a selected program) to the implantable stimulator 404. In one embodiment, the external telemetry circuit 640 also transmits power to the implantable stimulator 404 through inductive coupling.

The external communication device 620 provides a mechanism to conduct communications with a programming information source, such as a data service, program modeling system, or other aspects of a dynamic information system, to receive program information via an external communication link (not shown). As described in the following paragraphs, the program modeling system may be used to identify a program or program data to the external patient programming device 602 that corresponds to a new or different neurostimulation program or characteristics of a neurostimulation program (which is, in turn, selected to provide an improved treatment of a chronic pain condition by the dynamic model). The external communication device 620 and the programming information source may communicate using any number of wired or wireless communication mechanisms described in this document, including but not limited to IEEE 802.11 (Wi-Fi), Bluetooth, Infrared, and like standardized and proprietary wireless communications implementations. Although the external telemetry circuit 640 and the external communication device 620 are depicted as separate components within the external patient programming device 602, the functionality of both of these components may be integrated into a single communication chipset, circuitry, or device.

The external storage device 618 stores a plurality of existing neurostimulation waveforms, including definable waveforms for use as a portion of the pattern of the neurostimulation pulses, settings and setting values, other portions of a program, and related treatment efficacy indication values. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 618 can be definable at least in part by one or more parameters including, but not limited to the following: amplitude, pulse width, frequency, jduration(s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 618 also stores a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program (including settings changed as a result of evaluation with the dynamical information system and the dynamic models) may be correlated to the control of these waveforms and definable fields.

The programming control circuit 616 represents an embodiment of a programming control circuit 316 and generates the plurality of stimulation parameters, which is to be transmitted to the implantable stimulator 404, based on the pattern of the neurostimulation pulses. The pattern is defined using one or more waveforms selected from the plurality of individually definable waveforms (e.g., defined by a program) stored in an external storage device 618. In various embodiments, a programming control circuit 616 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to select, modify, enable, disable, activate, schedule, or otherwise define a program or sets of programs for use with the neurostimulation device and perform various other monitoring and programming tasks for operation of the neurostimulation device. The user interface device 610 can enable a user to implement, save, persist, or update a program including the program or program parameters recommended or indicated by the programming information source, such as a data service or program modeling system. The user interface device 610 includes a display screen 642, a user input device 644, and an interface control circuit 646. The display screen 642 may include any type of interactive or non-interactive screens, and the user input device 644 may include any type of user input devices that supports the various functions discussed in this document, such as a touchscreen, keyboard, keypad, touchpad, trackball, joystick, and mouse. The user interface device 610 may also allow the user to perform any other functions discussed in this document where user interface input is suitable.

Interface control circuit 646 controls the operation of the user interface device 610 including responding to various inputs received by the user input device 644 that define or modify characteristics of implementation (including conditions, schedules, and variations) of one or more programs, parameters within the program, characteristics of one or more stimulation waveforms within a program, and like neurostimulator operational values that may be entered or selected with the external patient programming device 602, or obtained from the programming information source, such as the data service, or the program modeling system. Interface control circuit 646 includes a neurostimulation program circuit 660 that may generate a visualization of such characteristics of implementation, and receive and implement commands to implement the program and the neurostimulator operational values (including a status of implementation for such operational values). These commands and visualization may be performed in a review and guidance mode, status mode, or in a real-time programming mode.

The controller 650 can be a microprocessor that communicates with the external telemetry circuit 640, the external communication device 620, the external storage device 618, the programming control circuit 616, and the user interface device 610, via a bidirectional data bus. The controller 650 can be implemented by other types of logic circuitry (e.g., discrete components or programmable logic arrays) using a state machine type of design. As used in this disclosure, the term "circuitry" should be taken to refer to either discrete logic circuitry, firmware, or to the programming of a microprocessor.

As will be understood, the variety of settings for a neurostimulation device may be provided by many variations of programming parameter settings within programs. Existing patient programmers only provide a limited ability for a patient to cycle through programs that have defined programming parameters, with hundreds or thousands of specific settings often being rolled up into a single program. The following system and methods provide technical mechanisms to generate and recommend new programs and parameters for chronic pain therapy in response to trust dynamics and observed trust characteristics. Based on the identification of trust measurements and pain susceptibility, the assessment of pain susceptibility can be leveraged to further tailor the delivery of neurostimulation settings to improve treatment for pain.

In an example, the trust measurements and pain susceptibility values are determined through the use of a chatbot or other automated/computer agent designed to engage a patient on a regular basis in interactions (e.g., person-to-agent communications). This chatbot is used to establish commitments with the patient, from which expectations and changes can be measured as a result of the fulfillment or violation of individual commitments or sets of commitments.

A variety of academic research has been conducted on understanding interactions between parties and estimating trust as a result of such interactions. Research has shown that a computational model of trust based on commitments may be utilized to determine the trust of one party relative to another, based on the interactions between the parties. In particular, commitments provide an important way to measure trust because such commitments can be easily identified from interpersonal interactions (by an objective outside observer) and can be used to easily classify or characterize the outcomes of interactions in high-level terms.

A simple example of a commitment used in a trust determination setting, provided in Kalia et al., *Güven: estimating trust from communications*, JOURNAL OF TRUST MANAGEMENT (2016) 3:1, is as follows: "A commitment C (debtor, creditor, antecedent, consequent) means that the debtor commits to bringing about the consequent for the creditor provided the antecedent holds. For example, C (Buck, Selia, deliver, pay) means that Buck (buyer) commits to Selia (seller) to paying a specified amount provided Selia delivers the goods. When Selia delivers, the commitment is detached. When Buck pays, the commitment is discharged or satisfied. If Selia delivers but Buck does not pay, the commitment is violated. In essence, a commitment describes a social relationship between two persons giving a high-level description of what one expects of the other. As a result, it is natural that commitments (and their satisfaction or violation) be useful as a basis for trust. In this example, if Buck discharges the commitment, he brings a positive experience to Selia and Selia's trust for Buck may increase; if Buck violates the commitment, he brings a negative experience to Selia and Selia's trust for Buck may decrease."

This commitment progression, and the results of creating, detaching, discharging, and canceling a commitment (and resulting fulfillments or violations of such a commitment) may be observed from various communications between a patient and another party (an agent) for the trust dynamics and pain management purposes described herein. The particular commitments and interactions that occur between the patient and the other party need not, however, discuss the neurostimulation medical treatment or pain condition of the patient. As a result, interactions and commitments may be made regarding topics that are entirely unrelated to neurostimulation or pain, even as the results of such interactions and commitments are observed to determine a trust condition used for neurostimulation treatment.

The relationship between trust and pain perception in a particular patient (and pain susceptibility, and the receptibility of analgesic treatment with neurostimulation) may be determined as a result of a cognitive disposition to trust from many patients. Specifically, whether a particular patient exhibits a level of trust—and the amount of trust that they exhibit towards a particular party, as contrasted with an amount of hostility or rejection—may be used as a derivative measurement or indicator for the potential efficacy of analgesic effect with a neurostimulation treatment. As a result, the tracking of a trust measurement value in time can be used longitudinally, or at cross sectional points, to optimize treatments and to determine whether the treatment is working, whether the treatment provides a beneficial result, or whether the treatment can be increased or modified to provide additional or more suitable amounts of treatment.

In a specific example, the trust measurement value discussed herein may be represented as an overall level or ratio of positive to negative outcomes. For instance, this trust measurement value may be mapped to commitment outcomes with the use of a ratio, defined as: (Positive)/(Positive+Negative), which defines a trust measurement value as a percentage of total interactions. In a specific example, a positive experience is defined as when an agent (e.g., chatbot) creates a commitment with the human subject, and the agent satisfies the commitment; whereas a negative experience is defined as when the agent violates the commitment to the human subject. In still further specific examples, the trust measurement value may be computed and weighted based on how severe the violation is, including by tracking the value relative to a base trust value or metric. Accordingly, the goal of the trust measurement value is to provide a measurement of the state of trusting of a particular human subject, as a feedback mechanism to estimate the particular suitability or benefit of a neurostimulation treatment or treatment change.

The following drawings illustrate example implementations of systems utilizing these or similar trust dynamics for the purpose of chronic pain treatment. It will be understood that variations to the pain and trust determination examples listed above, as used for the treatment of chronic pain with neurostimulation programs, are within the scope of the present disclosure.

Figure 7:
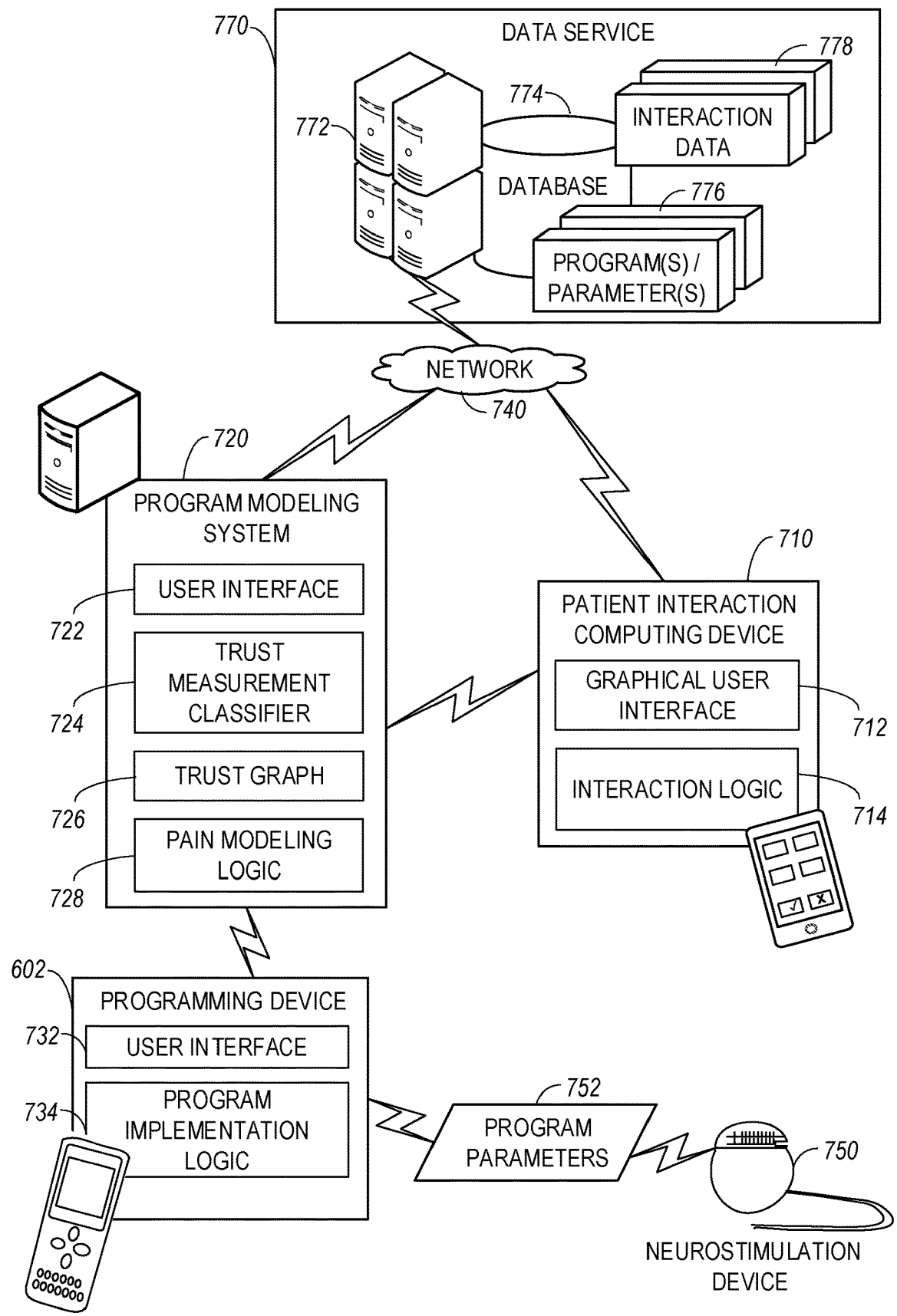
FIG. 7 illustrates, by way of example, an embodiment of data interactions among a programming device, a program modeling system, a patient interaction computing device, and a data service for selecting and implementing respective analgesic parameter settings for operation of a neurostimulation device based on trust dynamics.

FIG. 7 illustrates, by way of example, an embodiment of data interactions among a patient interaction computing device 710, a program modeling system 720, a programming device 602, and a data service 770 for selecting and implementing respective programs of defined parameter settings of a neurostimulation device, in connection with trust dynamics used to identify and deploy chronic pain treatments. The program modeling system 720 is shown in FIG. 7 in the form of a computing device (e.g., a server) with the computing device being specially programmed to communicate, over a network, the results of the modeled parameter settings and/or programs.

In an example, such program modeling may be performed through the evaluation of trust and pain values and settings, such as performed with: a trust measurement classifier 724 (e.g., with an algorithm implemented in software that is executed on the computing device to extract, identify, and determine a trust measurement value from patient interaction data); a trust graph 726 (e.g., with a data structure adapted to track and predict trust measurement values of a patient over time); and pain modeling logic 728 (e.g., with an algorithm implemented in software that is executed to determine the particular level of pain or pain susceptibility by the patient, based on the trust measurement or other trust values). The program modeling system 720 may also include a user interface 722 (e.g., in a software app interface, or an application programming interface) which provides the results of the trust measurement or pain measurements to another system or to a human user. It will be understood that other form factors and embodiments of the program modeling system 720, including in the integration of other programming devices, data services, or information services, may also be deployed.

In an example, the patient interaction computing device 710 is a computing device (e.g., personal computer, tablet, smartphone) or other form of user-interactive device (e.g., robot, AI device) which receives and provides interaction with a patient using a graphical user interface 712 and interaction logic 714. The specific outputs provided via the graphical user interface 712 may be defined and determined using the interaction logic 714, such as to facilitate various human-to-machine interactions in a communication session. Other form factors and interfaces such as smart speakers, audio interfaces, text interfaces, and the like may also be substituted for or augmented with the graphical user interface 712. In an example, the interaction logic 714 hosts one or more conversations with the patient using the graphical user interface 712, with such conversations involving the establishment, fulfillment, or violation of commitments and other trust-related interactions. Also in an example, the interaction logic 714 may be exposed by or host a chatbot or agent-based interface, through the use of the graphical user interface 712.

The program modeling system 720 (and in some examples, the programming device 602) may communicate to a data service 770 via a network 740 (e.g., a private local area network, public wide area network, the Internet, and the like) to obtain pre-defined programs, program settings, program modifications, constraints, rules, or like information related to programming (programs and parameters 776) or system operational data (e.g., interaction data 778). Such system operational data may be related to trust dynamics, trust measurement, pain susceptibility, and pain modeling for the particular patient or a set of patients. The data service 770, for example, may serve as a data service to host program information for a plurality of neurostimulation programs (e.g., across multiple patients, facilities, or facility locations) and model parameters. In an example, the data service 770 may be operated or hosted by a research institution, medical service provider, or a medical device provider (e.g., a manufacturer of the neurostimulation device) for managing data and settings for respective programs and parameters 776 and interaction data 778 among a plurality of clinical deployments or device types. The data service 770 may provide an interface to backend data components such as a data processing server 772 and a database 774, to host, track, and maintain a plurality of programs and parameters 776 and interaction data 778 and related settings. For instance, the programming data service 770 may be accessed using an application programming interface (API) or other remotely accessible interface accessible via the network 740.

In an example, program parameters 752 to update the parameter(s) or program(s) of the neurostimulation device 750 are generated, identified, or otherwise determined by the program modeling system 720, and then communicated to the neurostimulation device 750 by the programming device 602. In a further example, the pain modeling logic 728 of the program modeling system 720 results in selection of an entirely new program, or a customized or modified program, which is communicated in the program parameters 752. In this fashion, the programming device 602 may comprise a patient or clinician programmer device, which is operable with the user interface 732 and program implementation logic 734 to activate, deploy, select, define, edit, and modify parameter(s) or program(s) in a personal, home, clinical, or experimental setting. Finally, in some examples, the program parameters 752 may be directly communicated or activated from the program modeling system 720 rather than a programming device 602. The programming device 602 is illustrated in the form factor of a patient-operable remote control, but may be embodied in a number of other form factors, including in clinician-operated systems.

Figure 8:
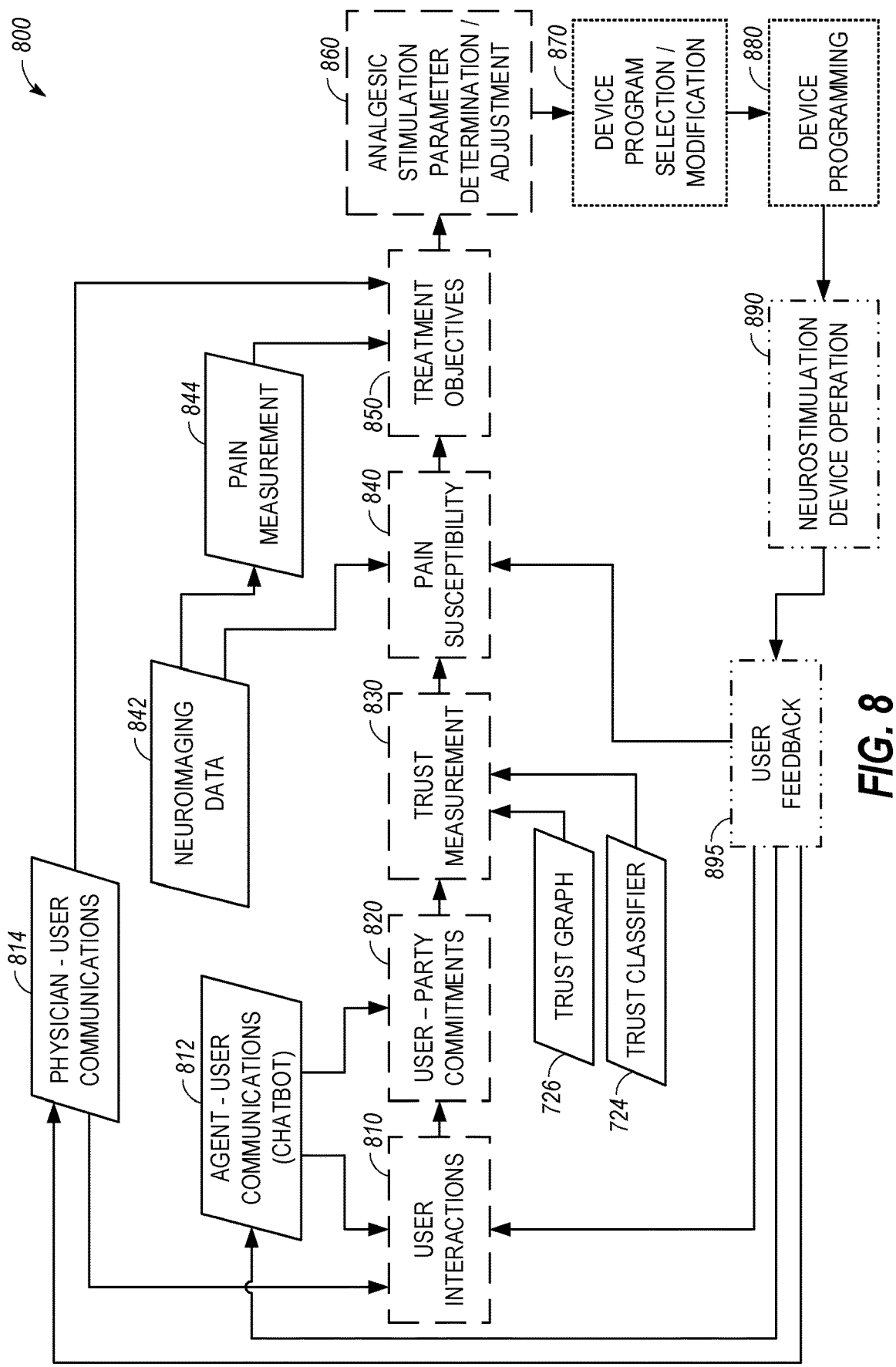
FIG. 8 illustrates, by way of example, an embodiment of functional components and data sets used in selecting and implementing respective analgesic parameter settings for operation of a neurostimulation device based on trust dynamics.

FIG. 8 illustrates, by way of example, a block diagram 800 of an embodiment of functional components and data sets used in selecting and implementing respective analgesic parameter settings for operation of a neurostimulation device based on trust dynamics. As shown, the block diagram 800 illustrates data flows among a series of sequential processing actions (810, 820, 830, 840, 850, 860) discussed below, followed by programming actions (870, 880) and operational actions (890, 895). It will be understood that these sequential actions may occur in the context of operations performed among the program modeling system 720, patient interaction computing device 710, and programming device 602, as referenced in FIG. 7 above, which identifies appropriate program parameters and settings for the neurostimulation device 750 using trust dynamics. However, the operations may be implemented in other settings and with other models, and accordingly, other data and processing flows may occur with variations of trust dynamics as described herein.

The sequential processing actions are depicted as commencing with user interactions 810, which are used to establish user-party commitments 820 involving aspects of trust fulfillment or violation. As discussed above, these user interactions and user-party commitments 820 may occur as a result of agent-user communications 812 with a chatbot (e.g., as provided in a graphical user interface 712 on the patient interaction computing device 710). The results of the commitments are used to produce a trust measurement value 830 or other trust representation.

In an example, the trust measurement value 830 is represented as a value between 0 to 1. In some examples, this value is scaled to 0 to 1, rounded up or down, or represented in another form. The trust measurement value 830 may be determined as a result of a trust measurement classifier 724 which predicts trust levels and classifies relevant inputs (e.g., commitment results and reactions, user interaction results) according to a trained or predetermined model. The trust measurement value 830 may also be represented in the context of the trust graph 726, which allows a state of trust to change and adapt over a period of time according to known values.

The trust measurement value 830 may be provided for further analysis to produce a pain susceptibility measurement value 840. This pain susceptibility measurement value 840 may be derived or a function of the trust measurement value 830 exclusively or as a result of other physiological data and observations. In a further example, the pain susceptibility measurement value 840 is enhanced as a result of a neuroimaging procedure that produces neuroimaging procedure data 842, such as medical imaging which is used to predict response to pain, treatment response, placebo effect, or which otherwise shows or predicts the effects of ongoing pain or neurostimulation relief. For example, a placebo effect measurement may be used to validate whether the trust metric has provided a proper prediction of treatment or treatment results.

The pain susceptibility measurement value 840 may be produced into treatment objectives 850 which may comprise or indicate various pain treatment approaches, areas for projected treatment, or other treatment-based indications relevant to the particular patient. The treatment objectives 850 may be further determined as a result of pain measurements 844 or other pain-related indications from the neuroimaging procedure data 842. Thus, the treatment objectives 850 may be produced as a result of pain modeling logic 728 which in turn may be correlated to any number of program modeling operations.

As a result of the treatment objectives 850, the pain modeling logic 728 may produce various types of analgesic stimulation parameter adjustments or values 860. These parameters in turn may be correlated to the selection or modification of a particular program that causes the neurostimulation device to implement the adjustments or values for improving analgesic effect in a patient. In some examples, the particular adjustments or values are tied to constraints and conditions such as safety or regulatory operation conditions, device engineering or operational limits, comfort or preference settings, or the like. Ultimately, the result of device programming 880 causes the selected or modified program or parameter to modify neurostimulation device operation 890.

In further examples, subsequent operation of the device, treatment, and trust dispositions may be used to coordinate user feedback 895 and further refinement of the neurostimulation parameters or program. As a result, the user feedback 895 (or other forms of monitoring) may modify the subsequent parameters of stimulation delivery based on a subsequent measure of trust disposition through subsequent user interactions 810 and subsequent agent-user communications 812. The user feedback 895 may also supply relevant values for a pain measurement or pain susceptibility measurement value 840. For instance, in some examples, the user feedback 895 may provide a feedback loop for a daily, weekly, or other regular monitoring and adjustment of neurostimulation.

The user feedback 895 may also be coordinated with physician-patient communications 814 as part of clinician oversight of the treatment process. In some examples, the physician-user communications 814 or other clinician oversight is used to affect or facilitate the user interactions 810, the pain susceptibility measurement value 840, the treatment objectives 850, or other variations in treatment and parameter determination.

Figure 9:
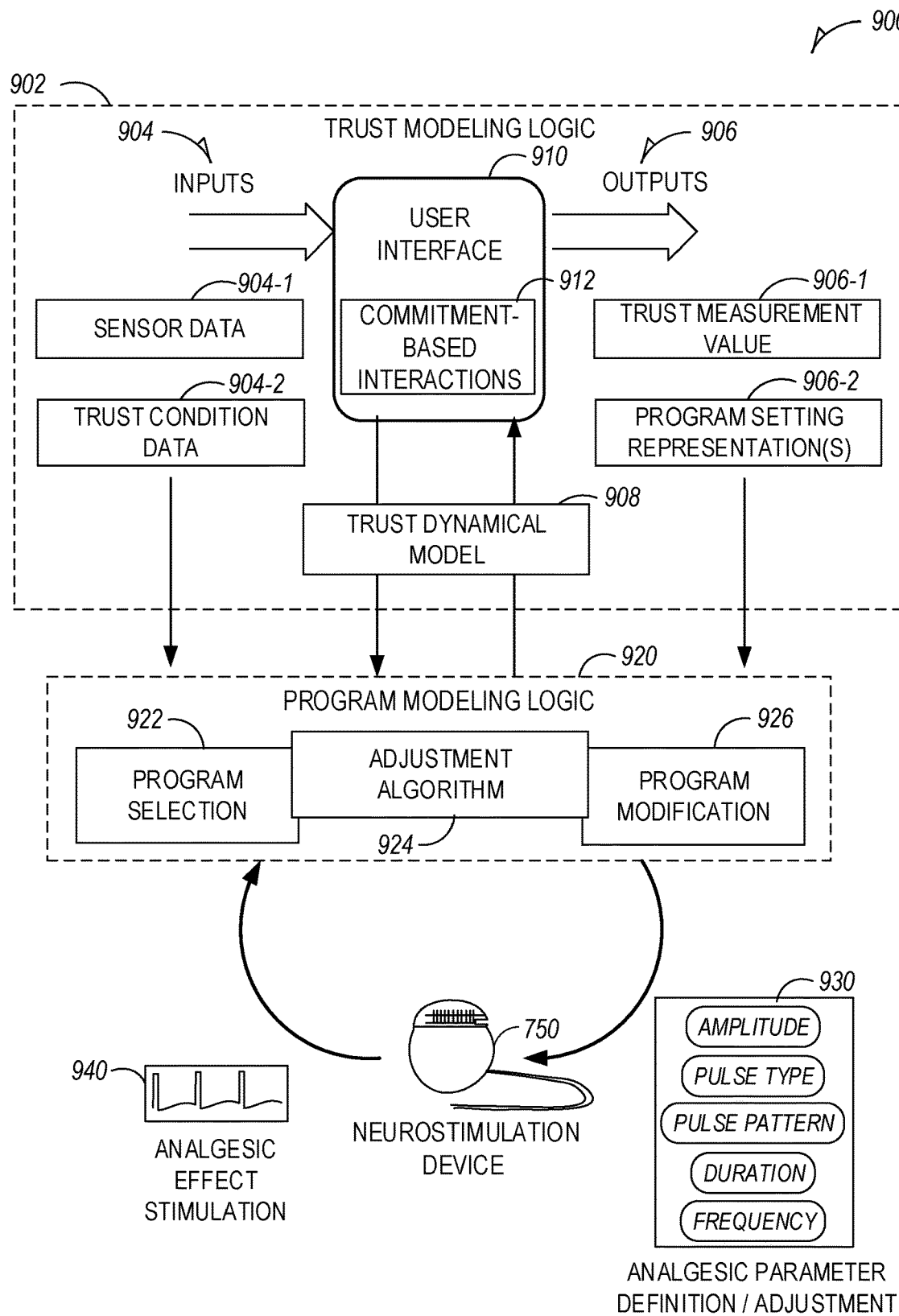
FIG. 9 illustrates, by way of example, an embodiment of a data and control flow between trust determination and neurostimulation program modeling operations, used in selecting and implementing respective analgesic parameter settings for operation of a neurostimulation device based on trust dynamics.

FIG. 9 illustrates, by way of example, an embodiment of a data and control flow 900 among trust modeling operations (with trust modeling logic 902) and neurostimulation program modeling (in a program modeling logic 920) operations, used in selecting and implementing respective analgesic parameter settings for operation of the neurostimulation device (e.g., the neurostimulation device 750) based on trust dynamics. As illustrated, the data and control flow 900 may involve a plurality of inputs 904 that are received, and a plurality of outputs 906 which are considered as part of the trust modeling logic 902. The results of these inputs and outputs are processed with the use of a trust dynamical model 908 that considers trust dynamics and measurements for use in neurostimulation programming and treatment.

In an example, the inputs 904 received within the trust modeling logic include sensor data 904-1 (e.g., physiological data from the neurostimulator device, or other medical monitoring devices) and trust condition data 904-2 (e.g., results, measurements, or values produced as a result of trust commitment violations and fulfillments). As suggested above, a user interface 910 may implement or be controlled by aspects of the trust modeling logic 902 to receive and facilitate the commitment-based interactions 912. The results of these interactions and the inputs 904 may be used to produce the outputs 906 including a trust measurement value 906-1, one or more program setting representations 906-2, and like values.

In an example, the program modeling logic 920 utilizes the results of the trust dynamical model 908 and other inputs and outputs from the trust modeling logic 902, to perform aspects of program selection 922, program modification 926, and other operational changes. Such modeling logic may involve use of an adjustment algorithm 924 which specifically is designed or modeled to implement changes based on the trust dynamics or other relevant trust modeling considerations.

As suggested above, the output of the programming modeling logic 920 may identify and effect the use of programming parameters 930 (e.g., device programming 880, and/or device program selection/modification 870) as part of treatment for a chronic pain condition using the neurostimulation device 750. As illustrated, the programming parameters 930 may include defined aspects such as amplitude, pulse type, pulse pattern, duration, and frequency, among other aspects described herein. The results of the definition and adjustment to the programming parameters 930 may result in specific analgesic effect stimulation 940 provided by the neurostimulation device. The results of this neurostimulation, and the feedback from this neurostimulation, may be further modified and updated in connection with the program modeling logic 920, trust modeling logic 902, and other system components or functions discussed above.

Figure 10:
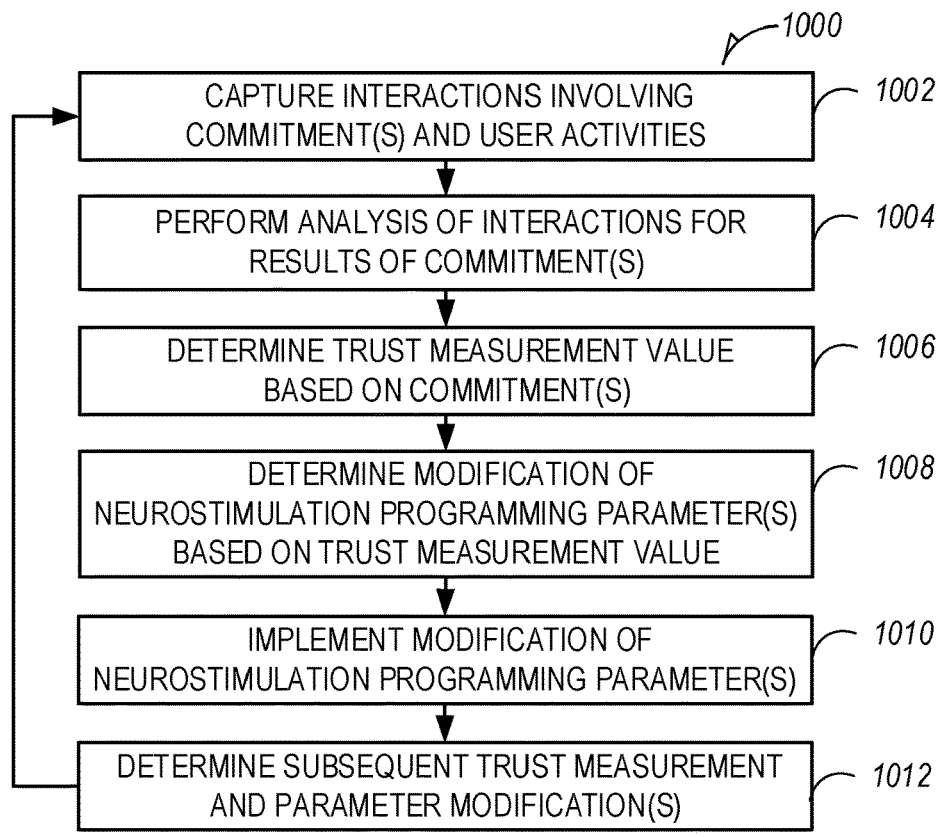
FIG. 10 illustrates, by way of example, an embodiment of a processing method implemented by a system or device for use to adjust programming of an implantable electrical neurostimulation device based on trust dynamics.

FIG. 10 illustrates, by way of example, an embodiment of a processing method 1000 implemented by a system or device for use to adjust programming of an implantable electrical neurostimulation device based on trust dynamics. For example, the processing method 1000 can be embodied by electronic operations performed by one or more computing systems or devices that are specially programmed to implement the trust measurement, program modeling, and neurostimulation programming functions described herein. In specific examples, the operations of the method 1000 may be implemented through the systems and data flows depicted above in FIGS. 7 to 9.

In an example, the method 1000 includes the capturing (e.g., receiving, requesting, extracting, processing) of interactions with a human subject (e.g., patient) involving one or more commitments and user activities (operation 1002). This may be followed by the performing of analysis of interactions between the human subject and another entity to determine the results of the one or more commitments (operation 1004). Such commitments may include those occurring from agent-user communications in a chatbot as discussed above for FIG. 8, although other communication formats and data forms may also be may be used. In an example, the interactions are performed with text or voice conversations occurring between the human subject and the another entity. For instance, the another entity may have created the commitment with the human subject and performed at least one observable action to cause the fulfillment or the violation of the at least one commitment.

As a result of the interactions and the analysis, a trust measurement value may be determined from the commitments (operation 1006). This trust measurement value may be derived or calculated from results of the one or more commitments (such as a reaction to a violation or fulfillment of the commitment) made with a human subject. In an example, the trust measurement value is derived from a reaction of the human subject in the interactions to specific fulfillment or violation events in the one or more commitments. Also in an example, the trust measurement value is determined with a classifier that performs analysis of the plurality of interactions for the fulfillment or the violation of the at least one commitment, such as with a classifier that is trained to predict a trust disposition for the human subject towards an other entity during the interactions. Also in an example, the trust measurement value is representable as a value within a trust graph, such that the trust graph provides a measurement of trust between the human subject and the other entity, based on evaluation of the human subject with the plurality of interactions over a period of time The method 1000 continues with a determination of a modification of at least one neurostimulation programming parameter of the implantable neurostimulation device, based on the trust measurement value (operation 1008). In an example, an amount of the modification of the neurostimulation programming parameter from a first state to a second state is correlated to an amount of change in the trust measurement value from a first state to a second state. In further examples (not depicted in the method 1000), the determination of the modification involves the use of other intermediate values, such as a pain susceptibility value based on the trust measurement value. For instance, a pain susceptibility value may be based on a prediction of the trust disposition for the human subject towards the other entity, with the pain susceptibility being used to determine the appropriate amount or type of programming modification. In further examples, this pain susceptibility is derived from a neuroimaging procedure performed on the human subject, such as with neuroimaging data that is used to determine a baseline to predict a placebo response of modification of a neurostimulation programming parameter.

The method 1000 concludes with the implementation of the modified neurostimulation programming parameters (operation 1010), such as with programming instructions, commands, or settings that cause a neurostimulation device to implement the parameters. Such parameters may implement or cause a change for one or more of: pulse patterns, pulse shapes, a spatial location of pulses, waveform shapes, or a spatial location of waveform shapes, for modulated energy provided with a plurality of leads of the implantable neurostimulation device. Such programming may be implemented in the manner as described with FIG. 7 above, or with other variations involving the use of patient, clinician, or administrator involvement.

Further operations and feedback as part of the method 1000 may continue with the estimation of subsequent trust measurements and parameter modifications (operation 1012), including the repeating of the operations 1002-1010 for a subsequent trust measurement value and parameter. In a specific example, the subsequent trust measurement metric may be determined from a series of interactions with the human subject conducted after the modification of the at least one neurostimulation programming parameter, and the subsequent modification and use of a programming parameter determined from the subsequent trust measurement metric.

Figure 11:
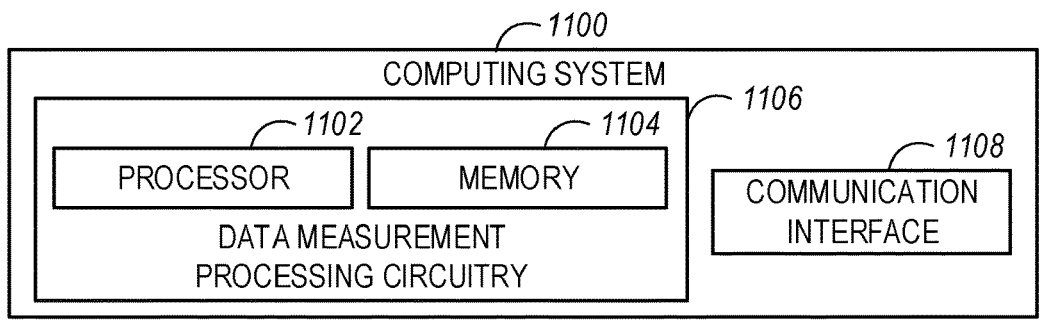
FIG. 11 illustrates, by way of example, a block diagram of an embodiment of a computing system implementing data measurement determination circuitry for use to adjust programming of an implantable electrical neurostimulation device for treating pain of a human subject.

FIG. 11 illustrates, by way of example, a block diagram of an embodiment of a system 1100 (e.g., a computing system) implementing data measurement determination circuitry for use to adjust programming of an implantable electrical neurostimulation device for treating pain of a human subject. The system 1100 may be a remote control device, patient programmer device, clinician programmer device, program modeling system, or other external device, usable for the adjustment of neurostimulation programming with the trust dynamic features discussed herein. In some examples, the system 1100 may be a networked device connected via a network (or combination of networks) to a programming device or programming service using a communication interface 1108, with the programming device or programming service providing output content for the graphical user interface or responding to input of the graphical user interface. The network may include local, short-range, or long-range networks, such as Bluetooth, cellular, IEEE 802.11 (Wi-Fi), or other wired or wireless networks.

The system 1100 includes a processor 1102 and a memory 1104, which can be optionally included as part of data measurement processing circuitry 1106. The processor 1102 may be any single processor or group of processors that act cooperatively. The memory 1104 may be any type of memory, including volatile or non-volatile memory. The memory 1104 may include instructions, which when executed by the processor 1102, cause the processor 1102 to implement the features of the user interface, or to enable other features of the data measurement processing circuitry 1106. Thus, electronic operations in the system 1100 may be performed by the processor 1102 or the circuitry 1106.

For example, the processor 1102 or circuitry 1106 may implement any of the features of the method 1000 (including operations 1002, 1004, 1006, 1012) to obtain and process data related to trust or pain state of a human subject, such as to determine a trust measurement value from results of at least one commitment made with a human subject, and determine a pain susceptibility value from such trust measurements or at least one commitment, as part of trust dynamics evaluated for a neurostimulation program or treatment. The system 1100 may save, output, or cause implementation of these measurements, directly or indirectly. It will be understood that the processor 1102 or circuitry 1106 may also implement other aspects of the logic and processing described above with reference to FIGS. 7-9.

Figure 12:
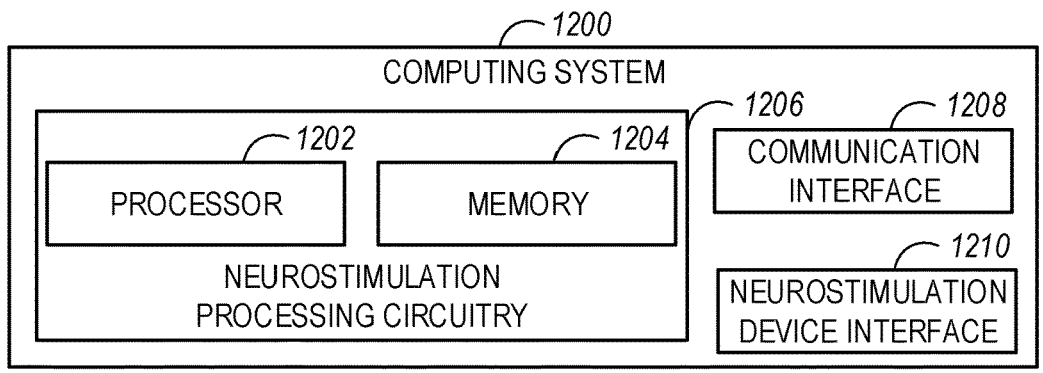
FIG. 12 illustrates, by way of example, a block diagram of an embodiment of a computing system implementing neurostimulation programming circuitry for use to establish programming of an implantable electrical neurostimulation device for treating pain of a human subject.

FIG. 12 illustrates, by way of example, a block diagram of an embodiment of a system 1200 (e.g., a computing system) implementing neurostimulation programming circuitry 1206 for use to adjust programming of an implantable electrical neurostimulation device for treating pain of a human subject. The system 1200 may be operated by a clinician, a patient, a caregiver, a medical facility, a research institution, a medical device manufacturer or distributor, and embodied in a number of different computing platforms. The system 1200 may be a remote control device, patient programmer device, program modeling system, or other external device, including a regulated device used to directly implement programming commands and modification with a neurostimulation device. In some examples, the system 1200 may be a networked device connected via a network (or combination of networks) to a computing system operating a user interface computing system using a communication interface 1208. The network may include local, short-range, or long-range networks, such as Bluetooth, cellular, IEEE 802.11 (Wi-Fi), or other wired or wireless networks.

The system 1200 includes a processor 1202 and a memory 1204, which can be optionally included as part of neurostimulation programming circuitry 1206. The processor 1202 may be any single processor or group of processors that act cooperatively. The memory 1204 may be any type of memory, including volatile or non-volatile memory. The memory 1204 may include instructions, which when executed by the processor 1202, cause the processor 1202 to implement the features of the neurostimulation programming circuitry 1206. Thus, the following references to electronic operations in the system 1200 may be performed by the processor 1202 or the circuitry 1206.

For example, the processor 1202 or circuitry 1206 may implement any of the features of the method 1000 (including operations 1008, 1010) to determine modification of neurostimulation programming parameters, implement (e.g., save, persist, activate, control) the programming parameters in the neurostimulation device, with use of a neurostimulation device interface 1210. The processor 1202 or circuitry 1206 may further provide data and commands to assist the processing and implementation of the programming using communication interface 1208. It will be understood that the processor 1202 or circuitry 1206 may also implement other aspects of the programming devices and device interfaces described above with reference to FIGS. 7-9.

Figure 13:
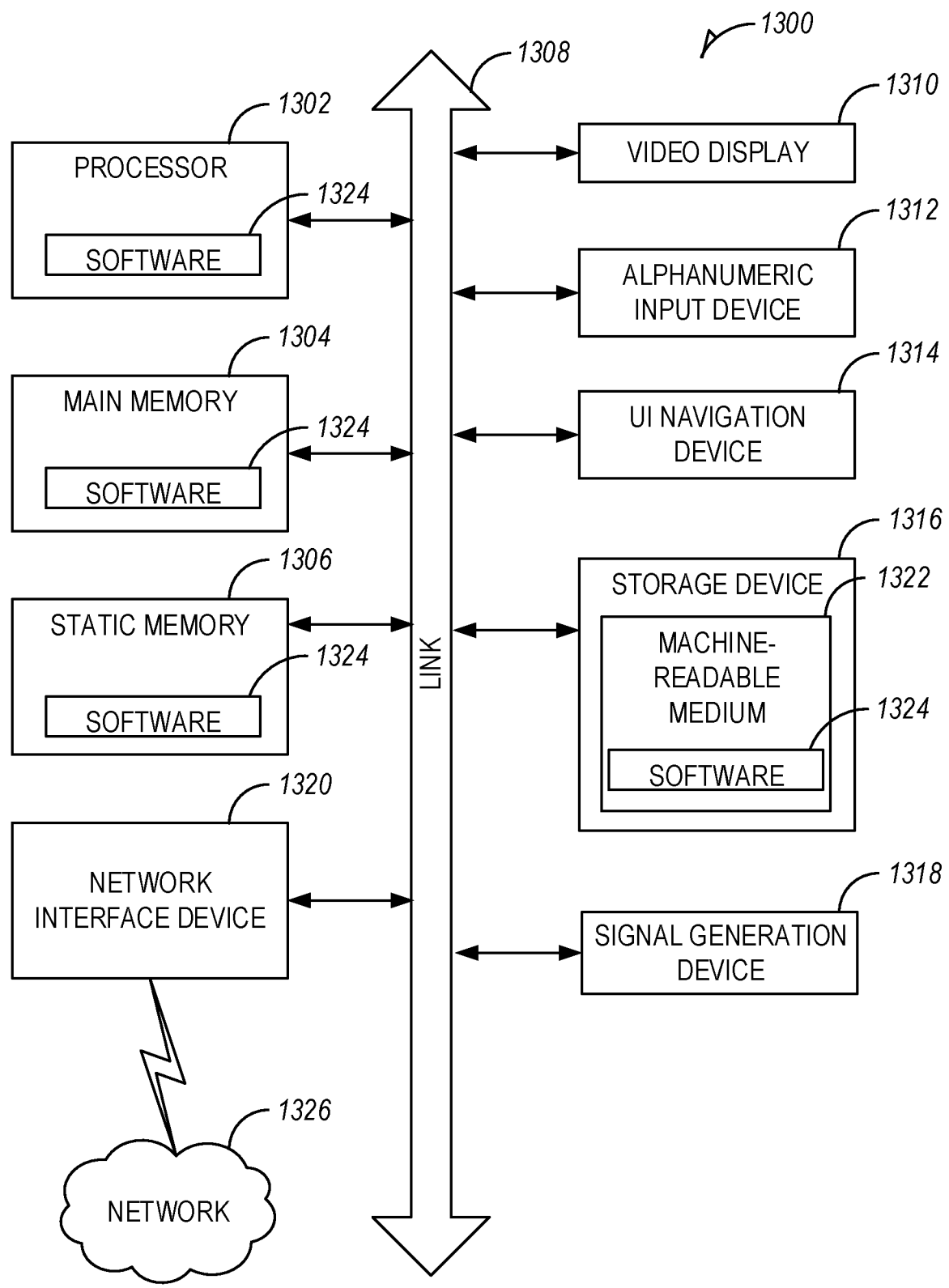
FIG. 13 is a block diagram illustrating a machine in the example form of a computer system, within which a set or sequence of instructions may be executed to cause the machine to perform any one of the methodologies discussed herein, according to an example embodiment.

FIG. 13 is a block diagram illustrating a machine in the example form of a computer system 1300, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1300 includes at least one processor 1302 (e.g., a central processing unit (CPU), a graphics processing unit (GPU) or both, processor cores, compute nodes, etc.), a main memory 1304 and a static memory 1306, which communicate with each other via a link 1308 (e.g., bus). The computer system 1300 may further include a video display unit 1310, an alphanumeric input device 1312 (e.g., a keyboard), and a user interface (UI) navigation device 1314 (e.g., a mouse). In one embodiment, the video display unit 1310, input device 1312 and UI navigation device 1314 are incorporated into a touch screen display. The computer system 1300 may additionally include a storage device 1316 (e.g., a drive unit), a signal generation device 1318 (e.g., a speaker), a network interface device 1320, and one or more sensors (not shown), such as a global positioning system (GPS) sensor, compass, accelerometer, or other sensor. It will be understood that other forms of machines or apparatuses (such as PIG, RC, CP devices, and the like) that are capable of implementing the methodologies discussed in this disclosure may not incorporate or utilize every component depicted in FIG. 13 (such as a GPU, video display unit, keyboard, etc.).

The storage device 1316 includes a machine-readable medium 1322 on which is stored one or more sets of data structures and instructions 1324 (e.g., software) embodying or utilized by any one or more of the methodologies or functions described herein. The instructions 1324 may also reside, completely or at least partially, within the main memory 1304, static memory 1306, and/or within the processor 1302 during execution thereof by the computer system 1300, with the main memory 1304, static memory 1306, and the processor 1302 also constituting machine-readable media.

While the machine-readable medium 1322 is illustrated in an example embodiment to be a single medium, the term "machine-readable medium" may include a single medium or multiple media (e.g., a centralized or distributed database, and/or associated caches and servers) that store the one or more instructions 1324. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1324 may further be transmitted or received over a communications network 1326 using a transmission medium via the network interface device 1320 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A computer system for determining programming of an implantable electrical neurostimulation device used for treating pain of a human subject, the system comprising:
 data processing circuitry configured to:
  receive a trust measurement value associated with a trust state of the human subject, the trust state based on outcomes of interactions between at least one entity and the human subject;

determine a treatment adjustment value associated with efficacy of pain treatment of the human subject, based on the trust measurement value; and generate at least one neurostimulation programming parameter of the implantable neurostimulation device, based on the treatment adjustment value; and neurostimulation programming circuitry configured to:

generate programming data for use with the implantable neurostimulation device, the programming data to cause the implantable neurostimulation device to implement the at least one neurostimulation programming parameter and provide the pain treatment to the human subject with neurostimulation using the at least one neurostimulation programming parameter.

2. The computer system of claim 1, wherein the treatment adjustment value is based on pain susceptibility or treatment susceptibility applicable to the human subject, and wherein the data processing circuitry further determines the pain susceptibility or the treatment susceptibility applicable to the human subject based on the outcomes of the interactions between the at least one entity and the human subject.

3. The computer system of claim 1, wherein the outcomes of the interactions include positive outcomes and negative outcomes, and wherein the trust measurement value provides a measurement of a level or ratio of the positive outcomes to the negative outcomes.

4. The computer system of claim 3, wherein the outcomes are evaluated from commitments having previously occurred between the at least one entity and the human subject, wherein the positive outcomes represent a fulfillment of respective commitments, and wherein the negative outcomes represent a violation of respective commitments.

5. The computer system of claim 1, wherein the trust state is represented by a data structure comprising a neural network or a graph, and wherein the trust measurement value is obtained from the data structure.

6. The computer system of claim 1, wherein the outcomes of the interactions are based on at least one electronic interaction involving text or voice conversations, and wherein the at least one entity includes a chatbot or automated agent.

7. The computer system of claim 1, wherein the programming data is generated by the neurostimulation programming circuitry using a program modeling system, wherein the program modeling system enables exploration of a set of possible neurostimulation programs and program settings based on feedback related to the trust state of the human subject and a treatment state of the human subject.

8. The computer system of claim 1, wherein the at least one neurostimulation programming parameter controls modulated energy provided with a plurality of leads of the implantable neurostimulation device, for one or more of:

pulse patterns, pulse shapes, a spatial location of pulses, waveform shapes, or a spatial location of waveform shapes.

9. The computer system of claim 8, the neurostimulation programming circuitry further configured to:

communicate the programming data to the implantable neurostimulation device, to create or update a neurostimulation program for the implantable neurostimulation device, wherein use of the neurostimulation program in the implantable neurostimulation device causes delivery of the modulated energy to the human subject.

10. A non-transitory machine-readable storage medium comprising instructions for determining programming of an implantable electrical neurostimulation device used for treating pain of a human subject, the instructions, when executed by circuitry of a machine, cause the machine to:

identify a trust measurement value associated with a trust state of the human subject, the trust state based on outcomes of interactions between at least one entity and the human subject;

determine a treatment adjustment value associated with efficacy of pain treatment of the human subject, based on the trust measurement value;

generate at least one neurostimulation programming parameter of the implantable neurostimulation device, based on the treatment adjustment value; and output programming data for use with the implantable neurostimulation device, the programming data to cause the implantable neurostimulation device to implement the at least one neurostimulation programming parameter and provide the pain treatment to the human subject with neurostimulation using the at least one neurostimulation programming parameter.

11. The machine-readable storage medium of claim 10, wherein the treatment adjustment value is based on pain susceptibility or treatment susceptibility applicable to the human subject, and wherein the instructions further to cause the machine to determine the pain susceptibility or the treatment susceptibility applicable to the human subject based on the outcomes of the interactions between the at least one entity and the human subject.

12. The machine-readable storage medium of claim 10, wherein the outcomes of the interactions include positive outcomes and negative outcomes, wherein the trust measurement value provides a measurement of a level or ratio of the positive outcomes to the negative outcomes, wherein the outcomes are evaluated from commitments having previously occurred between the at least one entity and the human subject, and wherein the positive outcomes represent a fulfillment of respective commitments, and wherein the negative outcomes represent a violation of respective commitments.

13. The machine-readable storage medium of claim 10, wherein the trust state is represented by a data structure comprising a neural network or a graph, and wherein the trust measurement value is obtained from the data structure.

14. The machine-readable storage medium of claim 10, wherein the programming data is generated by the machine using a program modeling system, wherein the program modeling system enables exploration of a set of possible neurostimulation programs and program settings based on feedback related to the trust state of the human subject and a treatment state of the human subject.

15. A method for determining programming of an implantable electrical neurostimulation device used for treating pain of a human subject, comprising:

identifying a trust measurement value associated with a trust state of the human subject, the trust state based on outcomes of interactions between at least one entity and the human subject;

determining a treatment adjustment value associated with efficacy of pain treatment of the human subject, based on the trust measurement value;

generating at least one neurostimulation programming parameter of the implantable neurostimulation device, based on the treatment adjustment value; and providing programming data for use with the implantable neurostimulation device, the programming data to cause the implantable neurostimulation device to implement the at least one neurostimulation programming parameter and provide the pain treatment to the human subject with neurostimulation using the at least one neurostimulation programming parameter.

16. The method of claim 15, wherein the treatment adjustment value is based on pain susceptibility or treatment susceptibility applicable to the human subject, and wherein the method further comprises determining the pain susceptibility or the treatment susceptibility applicable to the human subject based on the outcomes of the interactions between the at least one entity and the human subject.

17. The method of claim 15, wherein the outcomes of the interactions include positive outcomes and negative outcomes, wherein the trust measurement value provides a measurement of a level or ratio of the positive outcomes to the negative outcomes, wherein the outcomes are evaluated from commitments having previously occurred between the at least one entity and the human subject, and wherein the positive outcomes represent a fulfillment of respective commitments, and wherein the negative outcomes represent a violation of respective commitments.

18. The method of claim 15, wherein the trust state is represented by a data structure comprising a neural network or a graph, and wherein the trust measurement value is obtained from the data structure.

19. The method of claim 15, wherein the programming data is generated using a program modeling system, wherein the program modeling system enables exploration of a set of possible neurostimulation programs and program settings based on feedback related to the trust state of the human subject and a treatment state of the human subject.

20. The method of claim 15, wherein the programming data controls modulated energy provided with a plurality of leads of the implantable neurostimulation device, for one or more of: pulse patterns, pulse shapes, a spatial location of pulses, waveform shapes, or a spatial location of waveform shapes.

\* \* \* \* \*